(12) United States Patent
Multhoff

(10) Patent No.: US 7,517,948 B2
(45) Date of Patent: Apr. 14, 2009

(54) HSP70 PEPTIDE STIMULATING NATURAL KILLER (NK) CELL ACTIVITY AND USES THEREOF

(75) Inventor: Gabriele Multhoff, München (DE)

(73) Assignee: Multimmune GmbH, Regensburg (DE)

( * ) Notice: Subject to any disclaimer, the term of this patent is extended or adjusted under 35 U.S.C. 154(b) by 423 days.

(21) Appl. No.: 10/380,408

(22) PCT Filed: Sep. 13, 2001

(86) PCT No.: PCT/EP01/10593

§ 371 (c)(1),
(2), (4) Date: Aug. 25, 2003

(87) PCT Pub. No.: WO02/22656

PCT Pub. Date: Mar. 21, 2002

(65) Prior Publication Data

US 2004/0063173 A1 Apr. 1, 2004

(30) Foreign Application Priority Data

Sep. 13, 2000 (EP) .................... 00119933

(51) Int. Cl.
*C07K 5/00* (2006.01)
(52) U.S. Cl. .......................................... 530/300; 514/2
(58) Field of Classification Search ................. None
See application file for complete search history.

(56) References Cited

FOREIGN PATENT DOCUMENTS

| WO | 9949881 | | 10/1999 |
|---|---|---|---|
| WO | WO 97/28688 | * | 10/1999 |
| WO | 0031113 | | 6/2000 |
| WO | WO 00/31113 | * | 6/2000 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Bellone et al. (Immunology Today, v20 (10), 1999, pp. 457-461).*
Gura (Science, v278, 1997, pp. 1041-1042).*
Gabriele Multhoff, Claus Botzler and Rolf Issels; The Role of Heat Shock Proteins in the Stimulation of an Immune Response; Biol. Chem., vol. 379, pp. 295-300, Mar. 1998.

* cited by examiner

*Primary Examiner*—Christopher H Yaen
(74) *Attorney, Agent, or Firm*—Casimir Jones, S.C.

(57) ABSTRACT

The present invention relates to an immunostimulatory peptide derived from an Hsp70 protein and peptides comprising said immunostimulatory peptide. Furthermore the present invention pertains to polynucleotides encoding said peptide, vectors comprising said polynucleotides, fusion (poly)peptides comprising said peptide and compositions comprising said peptide. In addition the present invention relates to the use of said peptide, polynucleotide, vector or fusion (poly) peptide, for the preparation of pharmaceutical compositions for the treatment of diseases and for the stimulation of natural killer cell (NK cell) activity.

12 Claims, 8 Drawing Sheets

SEQUENCE LISTING

```
<160> NUMBER OF SEQ ID NOS: 8

<210> SEQ ID NO 1
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 1

Asn Leu Leu Gly Arg Phe Glu Leu
1               5

<210> SEQ ID NO 2
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 2
```

Asn Leu Leu Gly Arg Phe Glu Leu Ser Gly Ile Pro Pro
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 3

Thr Lys Asp Asn Asn Leu Leu Gly Arg Phe Glu Leu Ser Gly
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 4

Thr Lys Asp Asn Asn Leu Leu Gly Arg Phe Glu Leu
1               5                   10

<210> SEQ ID NO 5
<211> LENGTH: 641
<212> TYPE: PRT
<213> ORGANISM: Homo sapiens

<400> SEQUENCE: 5

Met Ala Lys Ala Ala Ile Gly Ile Asp Leu Gly Thr Thr Tyr Ser
1               5                   10                  15

Cys Val Gly Val Phe Gln His Gly Lys Val Glu Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Leu Asn Pro Gln
        50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

```
Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
            245                 250                 255

Lys Arg Ala Val Arg Arg Leu Arg Thr Ala Cys Glu Arg Ala Lys Arg
                260                 265                 270

Thr Leu Ser Ser Ser Thr Gln Ala Ser Leu Glu Ile Asp Ser Leu Phe
            275                 280                 285

Glu Gly Ile Asp Phe Tyr Thr Ser Ile Thr Arg Ala Arg Phe Glu Glu
        290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
        370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
        450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
        530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
        610                 615                 620

Gln Gly Pro Lys Gly Gly Ser Gly Ser Gly Pro Thr Ile Glu Glu Val
625                 630                 635                 640

Asp
```

<210> SEQ ID NO 6
<211> LENGTH: 650
<212> TYPE: PRT
<213> ORGANISM: Bos taurus

<400> SEQUENCE: 6

```
Met Ser Lys Gly Pro Ala Val Gly Ile Asp Leu Gly Thr Thr Tyr Ser
1               5                   10                  15
Cys Val Gly Val Phe Gln His Gly Lys Val Glu Ile Ile Ala Asn Asp
                20                  25                  30
Gln Gly Asn Arg Thr Thr Pro Ser Tyr Val Ala Phe Thr Asp Thr Glu
            35                  40                  45
Arg Leu Ile Gly Asp Ala Ala Lys Asn Gln Val Ala Met Asn Pro Thr
        50                  55                  60
Asn Thr Val Phe Asp Ala Lys Arg Leu Ile Gly Arg Arg Phe Asp Asp
65                  70                  75                  80
Ala Val Val Gln Ser Asp Met Lys His Trp Pro Phe Met Val Val Asn
                85                  90                  95
Asp Ala Gly Arg Pro Lys Val Gln Val Glu Tyr Lys Gly Glu Thr Lys
            100                 105                 110
Ser Phe Tyr Pro Glu Glu Val Ser Ser Met Val Leu Thr Lys Met Lys
        115                 120                 125
Glu Ile Ala Glu Ala Tyr Leu Gly Lys Thr Val Thr Asn Ala Val Val
    130                 135                 140
Thr Val Pro Ala Tyr Phe Asn Asp Ser Gln Arg Gln Ala Thr Lys Asp
145                 150                 155                 160
Ala Gly Thr Ile Ala Gly Leu Asn Val Leu Arg Ile Ile Asn Glu Pro
                165                 170                 175
Thr Ala Ala Ala Ile Ala Tyr Gly Leu Asp Lys Lys Val Gly Ala Glu
            180                 185                 190
Arg Asn Val Leu Ile Phe Asp Leu Gly Gly Gly Thr Phe Asp Val Ser
        195                 200                 205
Ile Leu Thr Ile Glu Asp Gly Ile Phe Glu Val Lys Ser Thr Ala Gly
    210                 215                 220
Asp Thr His Leu Gly Gly Glu Asp Phe Asp Asn Arg Met Val Asn His
225                 230                 235                 240
Phe Ile Ala Glu Phe Lys Arg Lys His Lys Lys Asp Ile Ser Glu Asn
                245                 250                 255
Lys Arg Ala Val Arg Arg Leu Arg Thr Ala Cys Glu Arg Ala Lys Arg
            260                 265                 270
Thr Leu Ser Ser Ser Thr Gln Ala Ser Ile Glu Ile Asp Ser Leu Tyr
        275                 280                 285
Glu Gly Ile Asp Phe Tyr Thr Ser Ile Thr Arg Ala Arg Phe Glu Glu
    290                 295                 300
Leu Asn Ala Asp Leu Phe Arg Gly Thr Leu Asp Pro Val Glu Lys Ala
305                 310                 315                 320
Leu Arg Asp Ala Lys Leu Asp Lys Ser Gln Ile His Asp Ile Val Leu
                325                 330                 335
Val Gly Gly Ser Thr Arg Ile Pro Lys Ile Gln Lys Leu Leu Gln Asp
            340                 345                 350
Phe Phe Asn Gly Lys Glu Leu Asn Lys Ser Ile Asn Pro Asp Glu Ala
        355                 360                 365
Val Ala Tyr Gly Ala Ala Val Gln Ala Ala Ile Leu Ser Gly Asp Lys
```

```
                    370                 375                 380
Ser Glu Asn Val Gln Asp Leu Leu Leu Asp Val Thr Pro Leu Ser
385                 390                 395                 400

Leu Gly Ile Glu Thr Ala Gly Gly Val Met Thr Val Leu Ile Lys Arg
                405                 410                 415

Asn Thr Thr Ile Pro Thr Lys Gln Thr Gln Thr Phe Thr Thr Tyr Ser
                420                 425                 430

Asp Asn Gln Pro Gly Val Leu Ile Gln Val Tyr Glu Gly Glu Arg Ala
            435                 440                 445

Met Thr Lys Asp Asn Asn Leu Leu Gly Lys Phe Glu Leu Thr Gly Ile
450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Ser Ala Val Asp Lys Ser Thr Gly
                485                 490                 495

Lys Glu Asn Lys Ile Thr Ile Thr Asn Asp Lys Gly Arg Leu Ser Lys
                500                 505                 510

Glu Asp Ile Glu Arg Met Val Gln Glu Ala Glu Lys Tyr Lys Ala Glu
            515                 520                 525

Asp Glu Lys Gln Arg Asp Lys Val Ser Ser Lys Asn Ser Leu Lys Ser
            530                 535                 540

Tyr Ala Phe Asn Met Lys Ala Thr Val Glu Asp Glu Lys Leu Gln Gly
545                 550                 555                 560

Lys Ile Asn Asp Glu Asp Lys Gln Lys Ile Leu Asp Lys Cys Asn Glu
                565                 570                 575

Ile Ile Asn Trp Leu Asp Lys Asn Gln Thr Ala Glu Lys Glu Glu Phe
                580                 585                 590

Glu His Gln Gln Lys Glu Leu Glu Lys Val Cys Asn Pro Ile Ile Thr
            595                 600                 605

Lys Leu Tyr Gln Ser Ala Gly Gly Met Pro Gly Gly Met Pro Gly Gly
            610                 615                 620

Met Pro Gly Gly Phe Pro Gly Gly Gly Ala Pro Pro Ser Gly Gly Ala
625                 630                 635                 640

Ser Ser Gly Pro Thr Ile Glu Glu Val Asp
                645                 650

<210> SEQ ID NO 7
<211> LENGTH: 641
<212> TYPE: PRT
<213> ORGANISM: Homo sapiens

<400> SEQUENCE: 7

Met Ala Thr Ala Lys Gly Ile Ala Ile Gly Ile Asp Leu Gly Thr Thr
1               5                   10                  15

Tyr Ser Cys Val Gly Val Phe Gln His Gly Lys Val Glu Ile Ile Ala
                20                  25                  30

Asn Asp Gln Gly Asn Arg Thr Thr Pro Ser Tyr Val Ala Phe Thr Asp
            35                  40                  45

Thr Glu Arg Leu Ile Gly Asp Ala Ala Lys Asn Gln Val Ala Met Asn
    50                  55                  60

Pro Gln Asn Thr Val Phe Asp Ala Lys Arg Leu Ile Gly Arg Lys Phe
65                  70                  75                  80

Asn Asp Pro Val Val Gln Ala Asp Met Lys Leu Trp Pro Phe Gln Val
                85                  90                  95
```

-continued

```
Ile Asn Glu Gly Gly Lys Pro Lys Val Leu Val Ser Tyr Lys Gly Glu
            100                 105                 110

Asn Lys Ala Phe Tyr Pro Glu Glu Ile Ser Ser Met Val Leu Thr Lys
        115                 120                 125

Leu Lys Glu Thr Ala Glu Ala Phe Leu Gly His Pro Val Thr Asn Ala
    130                 135                 140

Val Ile Thr Val Pro Ala Tyr Phe Asn Asp Ser Gln Arg Gln Ala Thr
145                 150                 155                 160

Lys Asp Ala Gly Val Ile Ala Gly Leu Asn Val Leu Arg Ile Ile Asn
                165                 170                 175

Glu Pro Thr Ala Ala Ala Ile Ala Tyr Gly Leu Asp Lys Gly Gly Gln
            180                 185                 190

Gly Glu Arg His Val Leu Ile Phe Asp Leu Gly Gly Gly Thr Phe Asp
        195                 200                 205

Val Ser Ile Leu Thr Ile Asp Asp Gly Ile Phe Glu Val Lys Ala Thr
    210                 215                 220

Ala Gly Asp Thr His Leu Gly Gly Glu Asp Phe Asp Asn Arg Leu Val
225                 230                 235                 240

Ser His Phe Val Glu Glu Phe Lys Arg Lys His Lys Lys Asp Ile Ser
                245                 250                 255

Gln Asn Lys Arg Ala Val Arg Arg Leu Arg Thr Ala Cys Glu Arg Ala
            260                 265                 270

Lys Arg Thr Leu Ser Ser Ser Thr Gln Ala Asn Leu Glu Ile Asp Ser
        275                 280                 285

Leu Tyr Glu Gly Ile Asp Phe Tyr Thr Ser Ile Thr Arg Ala Arg Phe
    290                 295                 300

Glu Glu Leu Cys Ala Asp Leu Phe Arg Gly Thr Leu Glu Pro Val Glu
305                 310                 315                 320

Lys Ala Leu Arg Asp Ala Lys Met Asp Lys Ala Lys Ile His Asp Ile
                325                 330                 335

Val Leu Val Gly Gly Ser Thr Arg Ile Pro Lys Val Gln Arg Leu Leu
            340                 345                 350

Gln Asp Tyr Phe Asn Gly Arg Asp Leu Asn Lys Ser Ile Asn Pro Asp
        355                 360                 365

Glu Ala Val Ala Tyr Gly Ala Ala Val Gln Ala Ala Ile Leu Met Gly
    370                 375                 380

Asp Lys Ser Glu Lys Val Gln Asp Leu Leu Leu Leu Asp Val Ala Pro
385                 390                 395                 400

Leu Ser Leu Gly Leu Glu Thr Val Gly Gly Val Met Thr Ala Leu Ile
                405                 410                 415

Lys Arg Asn Ser Thr Ile Pro Pro Lys Gln Thr Gln Ile Phe Thr Thr
            420                 425                 430

Tyr Ser Asp Asn Gln Pro Gly Val Leu Ile Gln Val Tyr Glu Gly Glu
        435                 440                 445

Arg Ala Met Thr Lys Asp Asn Asn Leu Leu Gly Arg Phe Asp Leu Thr
    450                 455                 460

Gly Ile Pro Pro Ala Pro Arg Gly Val Pro Gln Ile Glu Val Thr Phe
465                 470                 475                 480

Asp Ile Asp Ala Asn Gly Ile Leu Asn Val Thr Ala Thr Asp Lys Ser
                485                 490                 495

Thr Gly Lys Val Asn Lys Ile Thr Ile Thr Asn Asp Lys Gly Arg Leu
            500                 505                 510

Ser Lys Glu Glu Ile Glu Arg Met Val Leu Asp Ala Glu Lys Tyr Lys
```

```
                515                 520                 525
Ala Glu Asp Glu Val Gln Arg Glu Lys Ile Ala Ala Lys Asn Ala Leu
            530                 535                 540

Glu Ser Tyr Ala Phe Asn Met Lys Ser Val Val Ser Asp Glu Gly Leu
545                 550                 555                 560

Lys Gly Lys Ile Ser Glu Ser Asp Lys Asn Lys Ile Leu Asp Lys Cys
                565                 570                 575

Asn Glu Leu Leu Ser Trp Leu Glu Val Asn Gln Leu Ala Glu Lys Asp
            580                 585                 590

Glu Phe Asp His Lys Arg Lys Glu Leu Glu Gln Met Cys Asn Pro Ile
            595                 600                 605

Ile Thr Lys Leu Tyr Gln Gly Gly Cys Thr Gly Pro Ala Cys Gly Thr
            610                 615                 620

Gly Tyr Val Pro Gly Arg Pro Ala Thr Gly Pro Thr Ile Glu Glu Val
625                 630                 635                 640

Asp

<210> SEQ ID NO 8
<211> LENGTH: 638
<212> TYPE: PRT
<213> ORGANISM: Escherichia coli

<400> SEQUENCE: 8

Met Gly Lys Ile Ile Gly Ile Asp Leu Gly Thr Thr Asn Ser Cys Val
1               5                   10                  15

Ala Ile Met Asp Gly Thr Thr Pro Arg Val Leu Glu Asn Ala Glu Gly
            20                  25                  30

Asp Arg Thr Thr Pro Ser Ile Ile Ala Tyr Thr Gln Asp Gly Glu Thr
        35                  40                  45

Leu Val Gly Gln Pro Ala Lys Arg Gln Ala Val Thr Asn Pro Gln Asn
    50                  55                  60

Thr Leu Phe Ala Ile Lys Arg Leu Ile Gly Arg Arg Phe Gln Asp Glu
65                  70                  75                  80

Glu Val Gln Arg Asp Val Ser Ile Met Pro Phe Lys Ile Ile Ala Ala
                85                  90                  95

Asp Asn Gly Asp Ala Trp Val Glu Val Lys Gly Gln Lys Met Ala Pro
            100                 105                 110

Pro Gln Ile Ser Ala Glu Val Leu Lys Lys Met Lys Lys Thr Ala Glu
        115                 120                 125

Asp Tyr Leu Gly Glu Pro Val Thr Glu Ala Val Ile Thr Val Pro Ala
    130                 135                 140

Tyr Phe Asn Asp Ala Gln Arg Gln Ala Thr Lys Asp Ala Gly Arg Ile
145                 150                 155                 160

Ala Gly Leu Glu Val Lys Arg Ile Ile Asn Glu Pro Thr Ala Ala Ala
                165                 170                 175

Leu Ala Tyr Gly Leu Asp Lys Gly Thr Gly Asn Arg Thr Ile Ala Val
            180                 185                 190

Tyr Asp Leu Gly Gly Gly Thr Phe Asp Ile Ser Ile Ile Glu Ile Asp
        195                 200                 205

Glu Val Asp Gly Glu Lys Thr Phe Glu Val Leu Ala Thr Asn Gly Asp
    210                 215                 220

Thr His Leu Gly Gly Glu Asp Phe Asp Ser Arg Leu Ile Asn Tyr Leu
225                 230                 235                 240

Val Glu Glu Phe Lys Lys Asp Gln Gly Ile Asp Leu Arg Asn Asp Pro
```

-continued

```
                245                 250                 255
Leu Ala Met Gln Arg Leu Lys Glu Ala Ala Glu Lys Ala Lys Ile Glu
            260                 265                 270
Leu Ser Ser Ala Gln Gln Thr Asp Val Asn Leu Pro Tyr Ile Thr Ala
            275                 280                 285
Asp Ala Thr Gly Pro Lys His Met Asn Ile Lys Val Thr Arg Ala Lys
            290                 295                 300
Leu Glu Ser Leu Val Glu Asp Leu Val Asn Arg Ser Ile Glu Pro Leu
305                 310                 315                 320
Lys Val Ala Leu Gln Asp Ala Gly Leu Ser Val Ser Asp Ile Asp Asp
                325                 330                 335
Val Ile Leu Val Gly Gly Gln Thr Arg Met Pro Met Val Gln Lys Lys
                340                 345                 350
Val Ala Glu Phe Phe Gly Lys Glu Pro Arg Lys Asp Val Asn Pro Asp
                355                 360                 365
Glu Ala Val Ala Ile Gly Ala Ala Val Gln Gly Gly Val Leu Thr Gly
                370                 375                 380
Asp Val Lys Asp Val Leu Leu Leu Asp Val Thr Pro Leu Ser Leu Gly
385                 390                 395                 400
Ile Glu Thr Met Gly Gly Val Met Thr Thr Leu Ile Ala Lys Asn Thr
                405                 410                 415
Thr Ile Pro Thr Lys His Ser Gln Val Phe Ser Thr Ala Glu Asp Asn
                420                 425                 430
Gln Ser Ala Val Thr Ile His Val Leu Gln Gly Glu Arg Lys Arg Ala
                435                 440                 445
Ala Asp Asn Lys Ser Leu Gly Gln Phe Asn Leu Asp Gly Ile Asn Pro
                450                 455                 460
Ala Pro Arg Gly Met Pro Gln Ile Glu Val Thr Phe Asp Ile Asp Ala
465                 470                 475                 480
Asp Gly Ile Leu His Val Ser Ala Lys Asp Lys Asn Ser Gly Lys Glu
                485                 490                 495
Gln Lys Ile Thr Ile Lys Ala Ser Ser Gly Leu Asn Glu Asp Glu Ile
                500                 505                 510
Gln Lys Met Val Arg Asp Ala Glu Ala Asn Ala Glu Ala Asp Arg Lys
                515                 520                 525
Phe Glu Glu Leu Val Gln Thr Arg Asn Gln Gly Asp His Leu Leu His
                530                 535                 540
Ser Thr Arg Lys Gln Val Glu Glu Ala Gly Asp Lys Leu Pro Ala Asp
545                 550                 555                 560
Asp Lys Thr Ala Ile Glu Ser Ala Leu Thr Ala Leu Glu Thr Ala Leu
                565                 570                 575
Lys Gly Glu Asp Lys Ala Ala Ile Glu Ala Lys Met Gln Glu Leu Ala
                580                 585                 590
Gln Val Ser Gln Lys Leu Met Glu Ile Ala Gln Gln Gln His Ala Gln
                595                 600                 605
Gln Gln Thr Ala Gly Ala Asp Ala Ser Ala Asn Asn Ala Lys Asp Asp
                610                 615                 620
Asp Val Val Asp Ala Glu Phe Glu Glu Val Lys Asp Lys Lys
625                 630                 635
```

HSP70 PEPTIDE STIMULATING NATURAL KILLER (NK) CELL ACTIVITY AND USES THEREOF

Figure 1A:
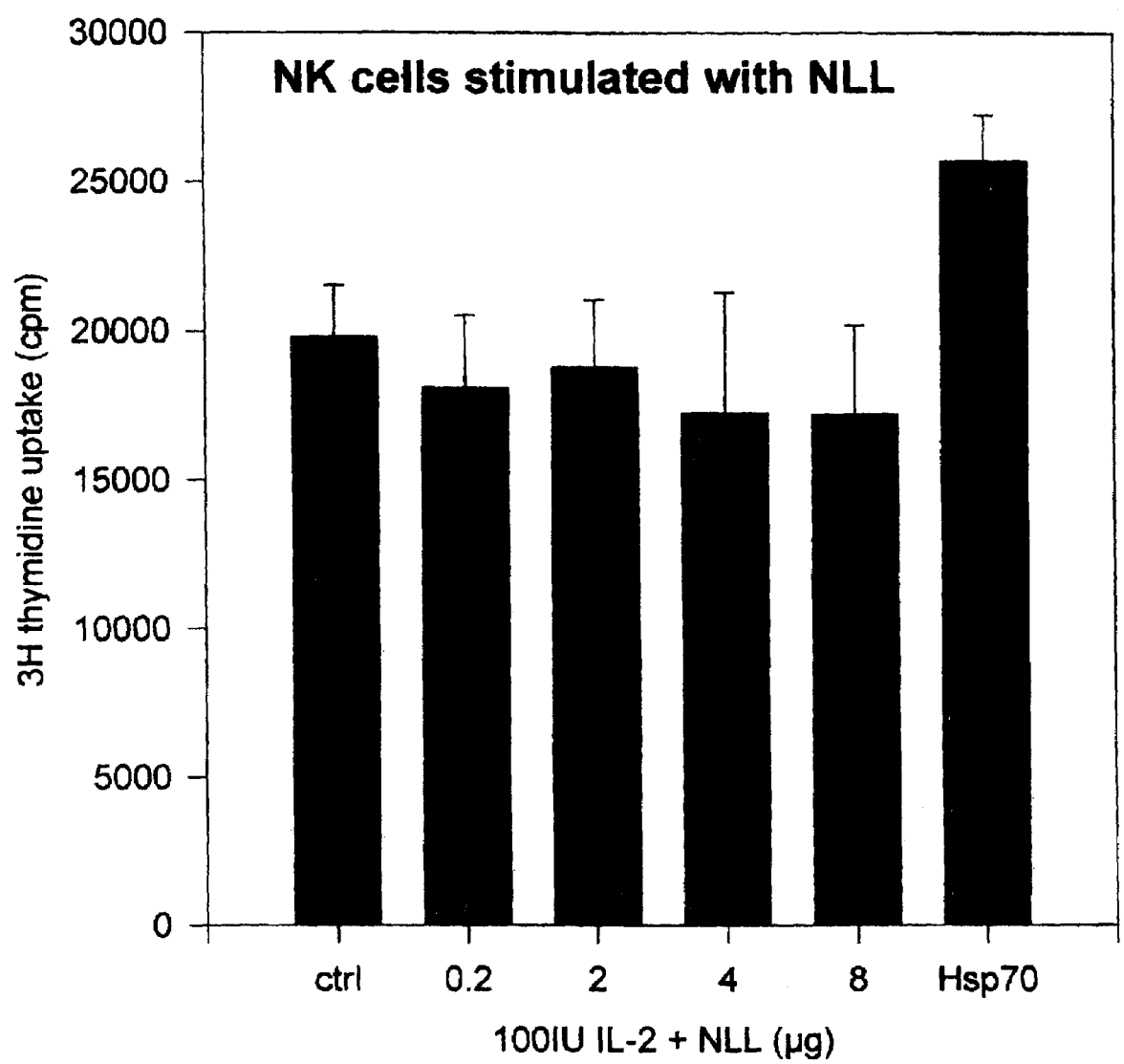

The present invention relates to an immunostimulatory peptide derived from an Hsp70 protein and peptides comprising said immunostimulatory peptide. Furthermore the present invention pertains to polynucleotides encoding said peptide, vectors comprising said polynucleotides, fusion (poly)peptides comprising said peptide and compositions comprising said peptide. In addition the present invention relates to the use of said peptide, polynucleotide, vector or fusion (poly) peptide, for the preparation of pharmaceutical compositions for the treatment of diseases and for the stimulation of natural killer cell (NK cell) activity.

Several documents are cited throughout the text of this specification. The disclosure content of each of the documents cited herein (including any manufacturer's specifications, instructions, etc.) is herewith incorporated herein by reference.

Heat shock proteins (HSP) are highly conserved proteins that are inducible by a variety of stressful stimuli and by physiological processes including cell differentiation and development (Lindquist and Craig. 1988). Intracellular HSP function as molecular chaperones, they are involved in protein folding, transport, antigen processing and presentation (DeNagel and Pierce, 1992; Hartl, 1996). HSP with a molecular weight of 70 and 90 kDa also have been shown to function as carrier proteins for immunogenic tumor-derived peptides that induce a T cell mediated immune response against cancer (Tamura et al., 1997; Schild et al., 1999; Srivastava et al., 1998). Antigen presenting cells are key for the receptor mediated uptake of HSP-peptide complexes (Arnold-Schild et al., 1999) Several groups reported an unusual plasma membrane localization of HSP on tumor cells (Altmeyer et al., 1996; Ferrarini et al., 1992; Piselli et al., 1995; Tamura et al., 1993). The inventors were the first who demonstrated that NK cells also have to be considered as relevant effector cells for the recognition of membrane-bound Hsp70 on tumor cells (Multhoff et al., 1995a, 1995b; Multhoff et al., 1997; Botzler et al., 1996a, 1996b). With respect to these findings and due to the fact that normal cells lack expression of Hsp70, the inducible member of the Hsp70 group on the plasma membrane, one might speculate that Hsp70 acts as a tumor-selective recognition structure for NK cells. Antibody blocking studies revealed that Hsp70 is a relevant recognition structure for transiently plastic adherent NK cells (Multhoff et al., 1995a, 1995b; Multhoff et al., 1997; Botzler et al., 1998). Although several antibodies detect membrane-bound Hsp70 on tumor cells, only the mAb RPN1197 was able to block the cytolytic activity of NK cells (Multhoff et al. 1995a).

It was recently demonstrated that proliferation and cytolytic activity of NK cells against Hsp70-expressing tumor cells could be stimulated with recombinant Hsp70 protein but not with HSc70 or DnaK (Multhoff et al. 1999). As target cells for the cytolytic activity of Nk cells the tumor sublines CX+ and CX− with an identical MHC and adhesion molecule expression pattern that differ with respect to the capacity to express Hsp70 on the plasma membrane, were used (Multhoff et al. 1997). It Was furthermore demonstrated that not only intact Hsp70 protein but also the C-terminal domain of Hsp70hom activates NK cells. Hsp70hom, a testis specific member of the HSp70 family, is 94% homologous to the C-terminal domain of Hsp70.

For the production of a (poly)peptide and its formulation in pharmaceutical compositions it is generally desirable to reduce its size as far as is reasonable with respect to its biological activity. A reduction in size and complexity increases the yield of a recombinantly expressed peptide and generally increases its chemical stability. When producing a peptide synthetically, yield and reliability of the process are also increased with a peptide of reduced size whereas production cost is minimized.

Therefore the technical problem underlying the present invention was to provide a small, easily obtainable molecule with immunostimulatory activity which can be produced synthetically or recombinantly in large amounts and at low cost. The solution to said technical problem is achieved by providing the embodiments characterized in the claims.

Accordingly, the present invention provides a peptide comprising or having the amino acid sequence TKDNNLLGRFELXG (SEQ ID NO:1) wherein X is T or S, wherein S is preferred (also throughout the further embodiments recited in this specification). The invention also encompasses fragments or derivatives of said peptide which will be explained further below.

The tern "peptide" as used herein denotes amino acid sequences comprising 30 or less amino acids.

It has surprisingly been found that a peptide comprising or having the sequence TKDNNLLGRFELXG (SEQ ID NO:1), wherein X is T or S, wherein S is preferred, is sufficient for the stimulation of NK cell activation. At least for in vitro purposes, an advantageous final concentration of the peptides has been found to be in the range of 0.2 to 2.5 ug/ml.

From the data available from the prior art it was not deducible that a peptide structure that encompasses hardly more than an antibody binding epitope might trigger such a complex cascade of events. In contrast, it was generally believed that a peptide alone is not sufficient to trigger T cell activation. The size of the-structure that was found sufficient to trigger such events excludes that cross-linking events are involved in the stimulation of NK activity by the underlying mechanism which, again, is surprising in view of the general beliefs of the prior art.

Comprised by the invention are also fragments and derivatives of the peptide of the invention wherein the derivatives have a different amino acid sequence which deviates from that of the peptide of the invention by substitution, insertion, deletion, duplication, inversion etc. provided that said fragments or derivatives stimulate NK cell activation. It is most preferred that in these peptides, amino acids TKDN (SEQ ID NO:2) in positions 450 to 453 (of Hsp70) R in position 458 and S in position 462 are retained. Said derivatives or fragments may be further derivatized by e.g. peptidomimetics as will be outlined below. They may also form part of a fusion protein as described below. The derivatives and fragments that are composed by the present invention may be tested, without undue burden for functionality and medical usefulness as described throughout this specification and as described in particular in the appended examples. The derivatives or fragments preferably have the length of at least 13 amino acids and are preferably not longer than 30 amino acids, more preferably not longer than 20 amino acids.

The present invention also relates a peptide as defined supra comprising or having the amino acid sequence EGERAMTKDNNLLGRFELXG (SEQ ID NO:3) wherein X is T or S. The invention also encompasses fragments or derivatives of said peptide which have the activation function and can be selected as described supra.

The peptide of the present invention may be linked to other (poly)peptide sequences or may be part of (a) fusion (poly) peptide(s). Such fusion (poly)peptides/fusion proteins may be engineered to improve the characteristics of said fragments, derivatives or variants. For example, further amino acids may be added to improve stability and/or persistence during purification, handling or storage processes or to improve stability, half-life and/or persistence in vitro and in host organisms and/or patients. Furthermore, the peptide of the invention may be fused to other proteins or peptides which play a role in immune responses or in their potential treatment. Within the scope of the present invention are also Molecules which comprise the peptide of the invention which are linked to marker molecules and/or marker amino acid sequences. Such sequences comprise but are not limited to peptide-tags, histidine-tags, fluorescence molecules, GFP, FLAG and GST.

Therefore, the invention furthermore relates to a fusion (poly)peptide comprising the peptide of the invention.

The invention also relates to a polynucleotide encoding the peptide of the invention or said fusion (poly)peptide comprising the peptide of the invention.

The polynucleotide as employed in accordance with this invention and encoding the above-described peptide may be, e.g., DNA, cDNA, RNA or synthetically produced DNA or RNA or a recombinantly produced chimeric nucleic acid molecule comprising any of those polynucleotides either alone or in combination.

In a further embodiment, the invention relates to a nucleic acid molecule of at least 15 nucleotides in length hybridizing with a polynucleotide as described above or with a complementary strand thereof. Specific hybridization occurs preferably under stringent conditions and implies no or very little cross-hybridization with nucleotide sequences encoding no or substantially different peptides. Such nucleic acid molecules may be used as probes and/or for the control of gene expression. Nucleic acid probe technology is well known to those skilled in the art who will readily appreciate that such probes may vary in length. Preferred are nucleic acid probes of 17 to 35 nucleotides in length. Of course, it may also be appropriate to use nucleic acids of up to 100 and more nucleotides in length. Therefore, the polynucleotides encoding the peptide of the invention may be used as nucleic acid probes to identify nucleic acids molecules encoding (poly)peptides different from HSP70 comprising the peptide of the invention. Such (poly)peptides may be useful tools for investigating different pathways which may be involved in the activation of NK cells. Said nucleic acid probes are also useful for various pharmaceutical and/or diagnostic applications. On the one hand, they may be used as PCR primers for the amplification of polynucleotides encoding the peptide of the invention. In this context they may serve as useful diagnostic tools to determine e.g. the expression level of (poly)peptides comprising the peptide of the invention thereby assessing or predicting the status of NK cell activity. Nucleic acid molecules employed in this preferred embodiment of the invention which are complementary to a polynucleotide as described above may also be used for repression of expression of a gene comprising such a polynucleotide, for example due to an antisense or triple helix effect or for the construction of appropriate ribozymes (see, e.g., EP-A1 0 291 533, EP A1 0 321 201, EP-A2 0 360 257) which specifically cleave the (pre)-mRNA of a gene comprising a polynucleotide as described herein above. Selection of appropriate target sites and corresponding ribozymes can be done as described for example in Steinecke, Ribozymes, Methods in Cell Biology 50, Galbraith et al. eds Academic Press, Inc. (1995), 449-460. Standard methods relating to antisense technology have also been described (Melani, Cancer Res. (1991), 2897-2901). Said antisense or triple helix effect as well as the construction of relevant ribozymes is/are partially useful in pharmaceutical compositions to be employed for the suppression of NK-cell activity, e.g., in autoimmune or inflammatory diseases, viral infections, sepsis, etc. Furthermore, the person skilled in the art is well aware that it is also possible to label such a nucleic acid probe with an appropriate marker for specific (Inter alia, diagnostic) applications, such as for the detection of the presence of a polynucleotide as described herein above in a sample derived from an organism.

The above described nucleic acid molecules may either be DNA or RNA or a hybrid thereof. Furthermore, said nucleic acid molecule may either contain, for example, thioester bonds and/or nucleotide analogues, commonly used in oligonucleotide anti-sense approaches. Said modifications may be useful for the stabilization of the nucleic acid molecule against endo- and/or exonucleases in the cell. Said nucleic acid molecules may be transcribed by an appropriate vector containing a chimeric gene which allows for the transcription of said nucleic acid molecule in the cell.

With respect to the nucleotide sequences characterized above, the term "hybridizing" in this context is understood as referring to conventional hybridization conditions, preferably such as hybridization in 50% formamide/6×SSC/0.1% SDS/ 100 μg/ml ssDNA, in which temperatures for hybridization are above 37° C. and temperatures for washing in 0.1×SSC/ 0.1% SDS are above 55° C. Most preferably, the term "hybridizing" refers to stringent hybridization conditions, for example such as described in Sambrook, Molecular Cloning A Laboratory Manual, Cold Spring Harbor Laboratory (1989) N.Y. Stringent hybridization conditions include hybridization at 65° C. in 0.2×SSC, 0.1% SDS.

In a further embodiment the invention pertains to a vector comprising the polynucleotide encoding the peptide of the invention.

Many suitable vectors are known to those skilled in molecular biology, the choice of which would depend on the function desired and include plasmids, cosmids, viruses, bacteriophages and other vectors used conventionally in genetic engineering. Methods Which are well known to those skilled in the art can be used to construct various plasmids and vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989), (1994). Alternatively, the polynucleotides and vectors of the invention can be reconstituted into liposomes for delivery to target cells. As discussed in further details below, a cloning vector was used to isolate individual sequences of DNA. Relevant sequences can be transferred into expression vectors where expression of a particular polypeptide is required. Typical cloning vectors include pBscpt sk, pGEM, pUC9, pBR322 and pGBT9. Typical expression vectors include pTRE, pCAL-n-EK, pESP-1, pOP13CAT.

Hence, in a preferred embodiment of the present invention the polynucleotides encoding the peptide of the invention either alone or present in a vector are linked to control sequences which allow the expression of the polynucleotide in prokaryotic and/or eukaryotic cells.

The term "control sequence" refers to regulatory DNA sequences which are necessary to effect the expression of coding sequences to which they are ligated. The nature of such control sequences differs depending upon the host organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is preferably used.

Thus, the vector of the invention is preferably an expression vector. An "expression vector" is a construct that can be used to transform a selected host cell and provides for expression of a coding sequence in the selected host. Expression vectors can for instance be cloning vectors, binary vectors or integrating vectors. Expression comprises transcription of the nucleic acid molecule preferably into a translatable mRNA. Regulatory elements ensuring expression in prokaryotic and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic host cells comprise, e.g., the $P_L$, lac, trp or tac promoter in *E. coli*, and examples of regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. In this context, suitable expression vectors are known in the art such as Okayama-Berg cDNA expression vector pcDV1 (Pharmacia), pCDM8, pRc/CMV, pcDNA1, pcDNA3 (In-vitrogene), pSPORT1 (GIBCO BRL). An alternative expression system which could be Used to express a cell cycle interacting protein is an insect system. In one such system, *Autographa californica* nuclear polyhedrosis virus (AcNPV) is used as a vector to express foreign genes in *Spodoptera frugiperda* cells or in *Trichoplusia* larvae. The coding sequence of a nucleic acid molecule of the invention may be cloned into a nonessential region of the virus, such as the polyhedrin gene, and placed under control of the polyhedrin promoter. Successful insertion of said coding sequence will render the polyhedrin gene inactive and produce recombinant virus lacking coat protein. The recombinant viruses are then used to infect *S. frugiperda* cells or Trichoplusia larvae in which the protein of the invention is expressed (Smith et al., 1983; Engelhard et al., 1994).

To obtain agents derived from the peptide of the present invention with a further increased stability and to improve the uptake via the gastrointestinal tract or other routes different from a parental application like e.g. skin or lung peptidomimetics may be utilized to design pseudopeptide analogues. A computer redesign of the structure of the peptide of the invention can be performed using appropriate computer programs (Olszewski et al., 1996; Hoffman et al., 1995). In particular, the appropriate programs can be used for the identification of interactive sites of the peptide and, if present, its receptor or other interacting proteins by computer assistant searches for complementary peptide sequences (Fassina, 1994). Further appropriate computer systems for the design of protein and peptides are described in the prior art, for example in Berry et al. (1994), Wodak et al., (1987) or Pabo et al. (1986). The results obtained from the above-described computer analysis can be used for, e.g., the preparation by peptidomimetics of the peptide of the invention. Such pseudopeptide analogues of the natural amino acid sequence of the peptide may very efficiently mimic the parent protein (Benkirane et al., 1996). For example, incorporation of easily available achiral Ω-amino acid residues into the peptide of the invention results in the substitution of amide bonds by polymethylene units of an aliphatic chain, thereby providing a convenient strategy for constructing a peptide by peptidbmimetics (Banerjee et al., 1996). Superactive peptidomimetic analogues of small peptide hormones in other systems are described in the prior art (Zhang et al., 1996). Appropriate peptidomimetics of the peptide of the present invention can also be identified by the synthesis of peptidomimetic combinatorial libraries through successive amide alkylation and testing the resulting compounds, e.g., for their immunological properties. Methods for the generation and use of peptidomimetic combihatorial libraries are described in the prior art, for example in Ostresh et al. (1996), and Dorner et al. (1996).

Furthermore, a three-dimensional and/or crystallographic structure of the peptide of the invention can be used for the design of peptidomimetic inhibitors of the biological activity of the protein of the invention (Rose et al., 1996; Rutenber et al., 1996).

The invention therefore also relates to a method of refining the peptide of the invention comprising (a) modeling said peptide by peptidomimetics and (b) chemically synthesizing the modeled peptide. A most suitable starting point for modeling by peptidomimetics is to test libraries of peptides of different lengths and sequences for stimulating NK-cell activation. By determining where (i.e. to which amino acid residues of which protein) the peptide of the invention binds to an NK-cell the crucial amino acids for binding within the peptide of the invention can be identified. In following steps, the peptide of the invention can be optimized by chemical modification so that a more efficient stimulation of NK-cell activation is achieved. Other putative NK cell activators can be modeled in the same way.

In another embodiment the present invention further relates to a composition comprising said peptide or a fragment or derivative thereof the polynucleotide encoding said peptide or a fragment or derivative thereof, a vector comprising said polynucleotide or a fusion (poly)peptide comprising said peptide or a fragment or derivative thereof and a pharmaceutically acceptable carrier and/or diluent.

The term "composition" as used herein also encompasses medical products and medical adjuvants and vaccines.

According to the invention, medical products are all substances or preparations used individually or in combination with each other of substances, or other subject-matters which, according to the producer, are meant to be applied to humans due to their functions for the purpose of detecting, preventing, monitoring, treating or alleviating diseases and whose main effect in or on the human body is achieved neither by pharmalogically or immunologically effective preparations nor by a metabolism whose effectiveriess may well be supported by such preparations.

According to the invention, medical adjuvants are such substances which are used for the production (as active ingredients) of pharmaceutical preparations or compositions.

In a preferred embodiment the composition is a pharmaceutical composition.

Said pharmaceutical composition advantageously also comprises a pharmaceutically acceptable carrier and/or diluent. It is additionally preferred that the pharmaceutical composition recited here or produced in accordance with further embodiments of this invention further comprises IL-2 and/or IL-18 in a suitable dose, preferably in a concentration of 1 ng to 1 µg/ml.

The term pharmaceutically acceptable carrier and/or diluent generally denotes vehicles commonly used to formulate pharmaceutical compositions for animal or human administration. The diluent is selected so as not to affect the biological activity of the combination. Examples of such diluents are sterile distilled water, physiological saline, Ringer's solutions, dextrose solution, Hank's solution, RPMI 1640 Medium and phosphate buffered saline (PBS). In addition, the pharmaceutical composition or formulation may also include other carriers, adjuvants, or nontoxic, nontherapeutic, nonimmunogenic stabilizers and the like. A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

Further examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment.

The compositions comprising, the peptide, compound drug, pro-drug or pharmaceutically acceptable salts thereof may conveniently be administered by any of the routes conventionally used for drug administration, for instance, orally, topically, parenterally or by inhalation. Acceptable salts comprise acetate, methylester, HCL, sulfate, chloride and the like. The drugs may be administered in conventional dosage forms prepared by combining the drugs with standard pharmaceutical carriers according to conventional procedures. The drugs and prodrugs identified and obtained in accordance with the present invention may also be administered in conventional dosages in combination with a known, second therapeutically active compound. Such therapeutically active compounds comprise, for example, those mentioned above. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof. The pharmaceutical carrier employed may be, for example, either a solid or liquid. Examplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, enulsions, various types of wetting agents, sterile solutions and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. When a liquid carrier is used, the preparation will be in the form of a syrup, emulsion, soft gelatin capsule, sterile injectable liquid such as an ampule or nonaqueaous liquid suspension.

The composition may be administered topically, that is by non-systemic administration. This includes the application externally to the epidermis or the buccal cavity and the instillation of such a compound into the ear, eye and nose, such that compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye which are suitable, for example, for use in UV protection. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

The composition in accordance with the present invention may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. The composition may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for compositions according to the invention, the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two to three times daily. The daily inhalation dosage regimen will preferably be from about 0.01 mg/kg to about 1 mg/kg per day. It will also be recognized by one of skill in the art that the optimal quantity and spacing of individual dosages of the compositions will be determined by the nature and extent of the condition being treated, the form, route and site of administration, and the particular patient being treated, and that such optimums can preferably be determined by the methods described herein. It will also be appreciated by one of skill in the art that the optimal course of treatment, i.e., the number of doses of the compositions given per day for a defined number of days, can be ascertained by those skilled in the art using conventional course of treatment determinations tests. The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

In another embodiment, the DNA sequence or vector of the invention, as described above, may be directly administered to a patient in need thereof. This type of administration is generally referred to as DNA vaccination. Routes for administration of gene vaccines are well known in the art and DNA vaccination has been successfully used to elicit alloimmune, anti-tumor and antiidiotype immune responses (Tighe M. et al., 1998). Moreover, inoculation with nucleic acid molecules/DNA has been found to be protective in different modes of viral disease (Fynan, et al., 1993; Boyer, 1997; Webster, et al., 1994; Montgomery et al., 1993; Barry, 1995; Xu and Liew, 1995; Zhong-et al., 1996; Luke et al., 1997; Mor, 1998; MacGregor et al., 1998).

The DNA encoding the peptide of the invention used in a pharmaceutical composition as a DNA vaccine may be formulated e.g. as neutral or salt form. Pharmaceutically acceptable salts, such as acid addition salts, and others, are known in the art. DNA vaccines are administered in dosages compatible with the method of formulation, and in such amounts that will be pharmacologically effective for prophylactic or therapeutic treatments. Preferably, the vaccine comprises an expression vector as described herein above.

Typically, vaccines are prepared as injectables, either as liquid solutions or suspensions; solid forms suitable for solution in or suspension in liquid prior to injection also may be prepared. The preparation may be emulsified or the protein may be encapsulated in liposomes. The active immunogenic ingredients often are mixed with pharmacologically acceptable excipients which are compatible with the active ingredient. Suitable excipients include but are not limited to water, saline, dextrose, glycerol, ethanol and the like; combinations of these excipients in various amounts also may be used. The vaccine also may contain small amounts of auxiliary substances such as wetting or emulsifying reagents, pH buffering agents, and/or adjuvants which enhance the effectiveness of the vaccine. For example, such adjuvants can include aluminum hydroxide, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphaosphoryloxy)-ethylamine (CGP 19835A, also referred to as MTP-PE), and RIBI (MPL+TDM+CWS) in a 2% squalene/Tween-80® emulsion.

The vaccines usually are administered by intravenous or intramuscular injection. Additional formulations which are suitable for other modes of administration include suppositories and, in some cases, oral or nasal formulations. For suppositories, traditional binders and carriers may include but are not limited to polyalkylene glycols or triglycerides. Oral formulation include such normally employed excipients as, for example, pharmaceutical grades of mannitol, lactose, starch, magnesium stearate, sodium saccharine, cellulose, magnesium carbonate and the like. These compositions may take the form of solutions, suspensions, tables, pills, capsules, sustained release formulations or powders and contain about 10% to about 95% of active ingredient, preferably about 25% to about 70%.

The peptide of the invention or a DNA encoding it are administered as a vaccine in a way compatible with the dosage formulation, and in such amounts as will be prophylactically and/or therapeutically effective. The quantity to be adminstered generally is in the range of about 0.2 nanograms to about 500 micrograms of peptide or DNA per dose, and depends upon the subject to be dosed, and the degree of immune-activation sought. Precise amounts of active ingredient required to be administered may also depend upon the judgment of the practitioner and may be unique to each subject. The peptide or DNA may be given in a single or multiple dose schedule. A multiple dose is one in which a primary course of vaccination may be with one to ten separate doses, followed by other doses given at subsequent time intervals required to maintain and/or to reinforce the immune response, for example, at one week to four months for a second dose, and if required by the individual, subsequent dose(s) weekly or monthly. The dosage regimen also will be determined, at least in part, by the need of the individual, and be dependent upon the practitioner's judgment. It is contemplated that the vaccine containing the immunogenic compounds of the invention may be administered in conjunction with other immunoregulatory agents, for example, with immunoglobulins or with cytokines.

In another embodiment the method of the invention relates to a method of producing a immunostimulatory peptide comprising
(a) mutating on the DNA or amino acid level a DNA molecule encoding or peptide comprising the sequence TKDNNLLGRFELXG (SEQ ID NO:1), Wherein X is T or S, in one or more nucleotide or amino acid positions;
(b) testing the proliferative response of NK cells to stimulation with IL-2 and/or IL18 together with the mutated peptide;
(c) comparing the proliferative response of NK cells to IL-2 and/or IL-18 together with the mutated peptide to the proliferative response to IL-2 and/or IL-18 without the mutated peptide or with a peptide having the sequence recited in (a);
(d) selecting a peptide comprising the mutated sequence or a recombinant DNA molecule coding for a peptide comprising the mutated sequence, wherein said mutated peptide displays an increase in the proliferative response as compared to IL-2 and/or IL-18 without the mutated peptide or with a sequence recited in (a) in step (c).

If nucleotides are mutated (i.e. exchanged by different naturally or non naturally occurring nucleotides), it is understood that at least one exchange should lead to an exchange on the amino acid level. It is most preferred that in these peptides, amino acids TKDN (SEQ ID NO:2) in positions 450 to 453 (of Hsp70) R in position 458 and S in position 462 are retained.

The term "proliferative response of NK cells" as used herein denotes proliferation of an NK cell population which can be determined by standard proliferation assays. Such assays comprise the measurement of incorporation of bromodeoxyuridine (BrdU) or thymidine into the cellular genome during S-phase as mentioned in the examples below. The percentage of increase should at least be 10%, preferably at least 20%, more preferably at least 50%. If the proliferative response of the mutated peptide is compared to the peptide having the sequence recited in (a), and an increase is observed, then a compound with an improved stimulatory activity may be selected.

In the method of the invention, the DNA sequence may be mutated upon which the peptide is expressed in a recombinant host such as E. coli, a mammalian or other cell. For this, the DNA sequence is usually expressed in a vector.

In a further embodiment the product is refined by computer redesign and/or peptidomimetics.

The invention also relates to a method of producing a pharmaceutical composition, medical product, medical adjuvant or vaccine comprising the step of formulating the peptide or recombinant DNA molecule selected by the method Of the invention with a pharmaceutically acceptable carrier and/or diluent.

The invention further relates to a method of producing a pharmaceutical composition comprising a molecule stimulating the activation of NK cells comprising the steps of (a) modifying the peptide of the invention as a lead compound to achieve (i) modified site of action, spectrum of activity, organ specificity, and/or (ii) improved potency, and/or (iii) decreased toxicity (improved therapeutic index), and/or (iv) decreased side effects, and/or (v) modified onset of therapeutic action, duration of effect, and/or (vi) modified pharmakinetic parameters (resorption, distribution, metabolism and excretion), and/or (vii) modified physico-chemical parameters (solubility, hygroscopicity, color, taste, odor, stability, state), and/or (viii) improved general specificity, organ/tissue specificity, and/or (ix) optimized application form and route by (i) esterification of carboxyl groups, or (ii) esterification of hydroxyl groups with carbon acids, or (iii) esterification of hydroxyl groups to, e.g. phosphates, pyrophosphates or sulfates or hemi succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetales, or (xiv) N-acetylation to amides, phenylcarbamates, or (xv) synthesis of Mannich bases, imines, or (xvi) transformation of ketones Or aldehydes to Schiffs bases, oximes, acetales, ketales, enolesters, oxazolidines, thiozolidines or combinations thereof; and (b) formulating the product of said modification with a pharmaceutically acceptable carrier.

The various steps recited above are generally known in the art. They include or rely on quantitative structure-action relationship (QSAR) analyses (Kubinyi, 1993), combinatorial biochemistry, classical chemistry and others (see, for example, Holzgrabe and Bechtold, 2000).

In a another embodiment the invention relates to a method for producing a pharmaceutical composition, medical product, medical adjuvant or vaccine comprising formulating the product obtained by the above method of the invention with a pharmaceutically acceptable carrier and/or diluent.

Employing the data obtainable with the peptide of the invention, new immunostimulatory substances may be generated. The sequence of the peptide of the invention provided herein allows to design modified or alternative molecules with immunostimulatory activity. In one alternative, potential immunostimulatory substances may be tested for on natural NK cells. Those substances which, in cotreatment with IL-2 and/or IL-18, stimulate a proliferate response which is higher than the proliferative response to IL-2 and/or IL-18 alone are to be formulated into pharmaceutical compositions for the downstream development of immunostimulatory substances suitable for formulation into pharmaceutical compositions. The new stimulatory substances may be further refined by peptidomimetics or otherwise as is known in the art, i.a. depending on the specific medical purpose or route of administration or may be prepared as a fusion protein. The embodiments recited in this paragraph also belong to the present invention.

Preferred concentrations of IL-2 and/or IL-18 are in the range of 1 ng-1 μg/ml.

Insofar, the invention relates also to a preferred method as stated above, wherein said product is refined by computer redesign and/or peptidomimetics.

In a still further embodiment the invention relates to the use of the peptide of the present invention the fusion (poly)peptide of the invention, the polynucleotide of the invention, the vector of the invention or the peptide refined by the method of the invention or to be formulated into a pharmaceutical composition produced by the method of the invention for the preparation of a pharmaceutical composition for the activation of NK cells.

The term "INK cells" ("natural killer cells") as used herein denotes large granular lymphocytes having CD45 surface expression and which furthermore have killer cell activity without previous stimulation. NK cells are especially characterized by epression of CD16 and/or by their susceptibility to Interleukin-2 stimulation and/or do not express CD3 and/or do not express α/β-γ/δ-T-cell receptors.

NK cells of the present invention preferably are further characterized by the following characteristics:
- they are transiently plastic-adherent after stimulation with IL-2 in a dosage of 10 to 10.000 units, e.g. von 100 units, wherein IL-2 can be obtained from Chiron Corp.;
- Adherens can be observed 3-18 h after stimulation of previously isolated PBLs (Peripheral Blood Lymphocytes) with IL-2;
- the NK cells express CD16dim (the mean value of fluorescence is weak);
- the NK cells express CD56 and CD57 as typical NK-markers;
- the NK-cells express CD94 (C-type lectin killer-cell-receptor);
- the NK-cells secrete IFNgamma after atceivation with Hsp70 and cytokines;
- the NK-cells can be activated (growth and cytotoxic activity) by Hsp70 (purified protein);
- they are not dependent on a patients MHC-type.

In the present invention different NK-cell populations can be applied. It is, however, required that the NK-cells as characterized herein can be activated by the peptide of the invention. It is possible to use isolated NK-cells but mixtures containing different cell types like peripheral blood mononuclear cells (PBMC) also comprising NK cells can be applied too.

In a preferred embodiment said activation comprises the activation of the proliferation of NK cells and/or the cytolytic activity of NK cells.

In a final embodiment the invention relates to the use of the peptide of the invention the fusion (poly)peptide of the invention, the polynucleotide of the invention, the vector of the invention or the peptide refined by the method of the invention or to be formulated into a pharmaceutical composition produced by the method of the invention for the preparation of a pharmaceutical composition in immunotherapy and/or for the treatment of diseases selected from carcinomas of lung, colorectum, pancreas, larynx, stomach, peripheral and central nervous system, other carcinomas, sarcomas, chronic myeloic leukemia (CML), acute myeloic leukemia (AML), acute lymphatic leukemia (ALL), non Hodgkin Lymphoma (NHL), myeloproliferative syndrome (MPS), myelodysplastic syndrome (MDS), plasmocytoma, other leukemias, other malignant diseases, wherein Hsp70 is present on the surface of malignant cells, an infection with an HI virus, other viral or bacterial infections Wherein Hsp70 is present on the surface of infected cells, rheumatoid arthritis, lupus erythematodes, other autoimmune diseases, asthma bronchiale, or other inflammatory diseases.

The figures show:

FIG. 1.

Figure 1B:
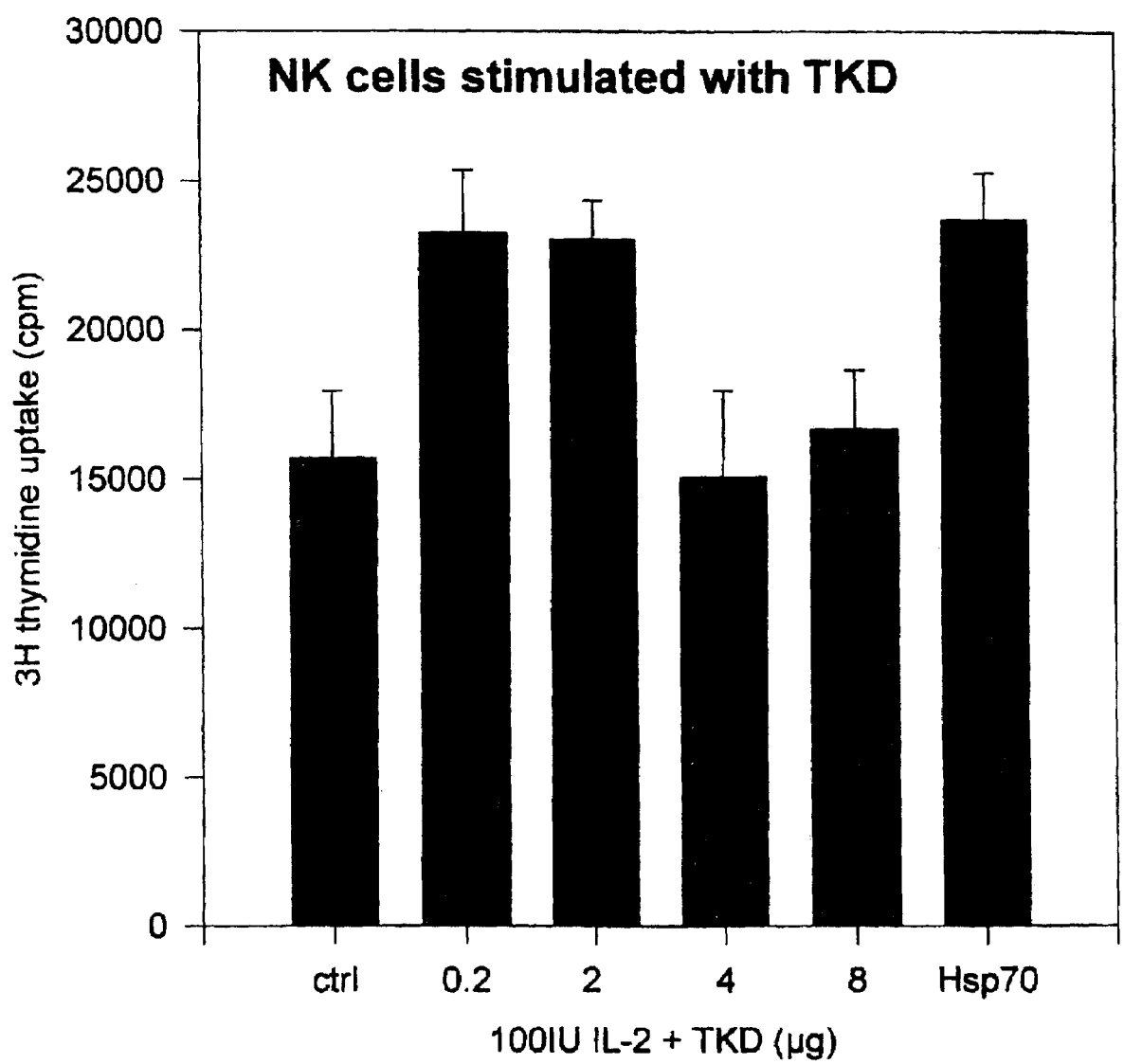
Figure 1C:
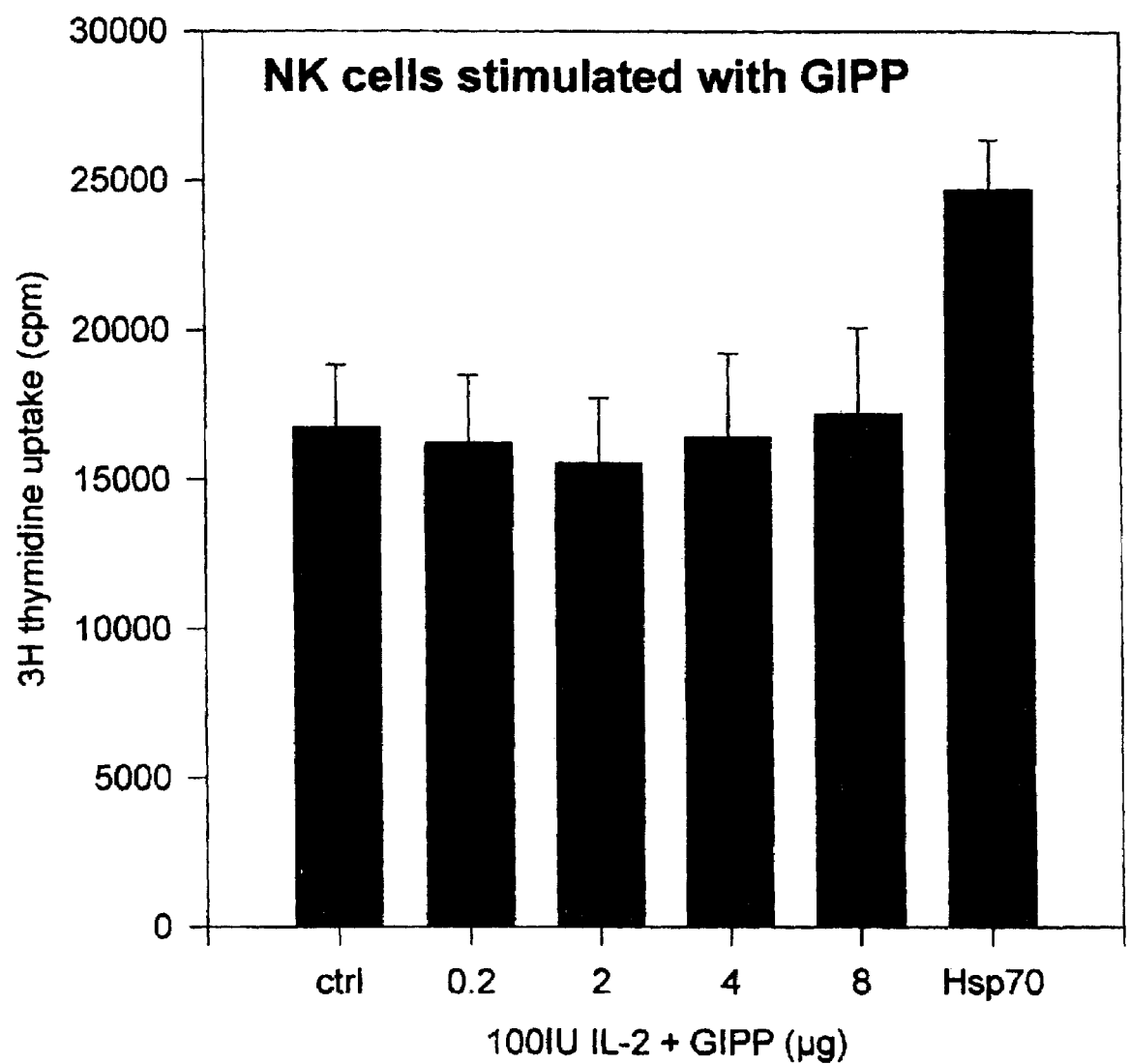
Figure 1D:
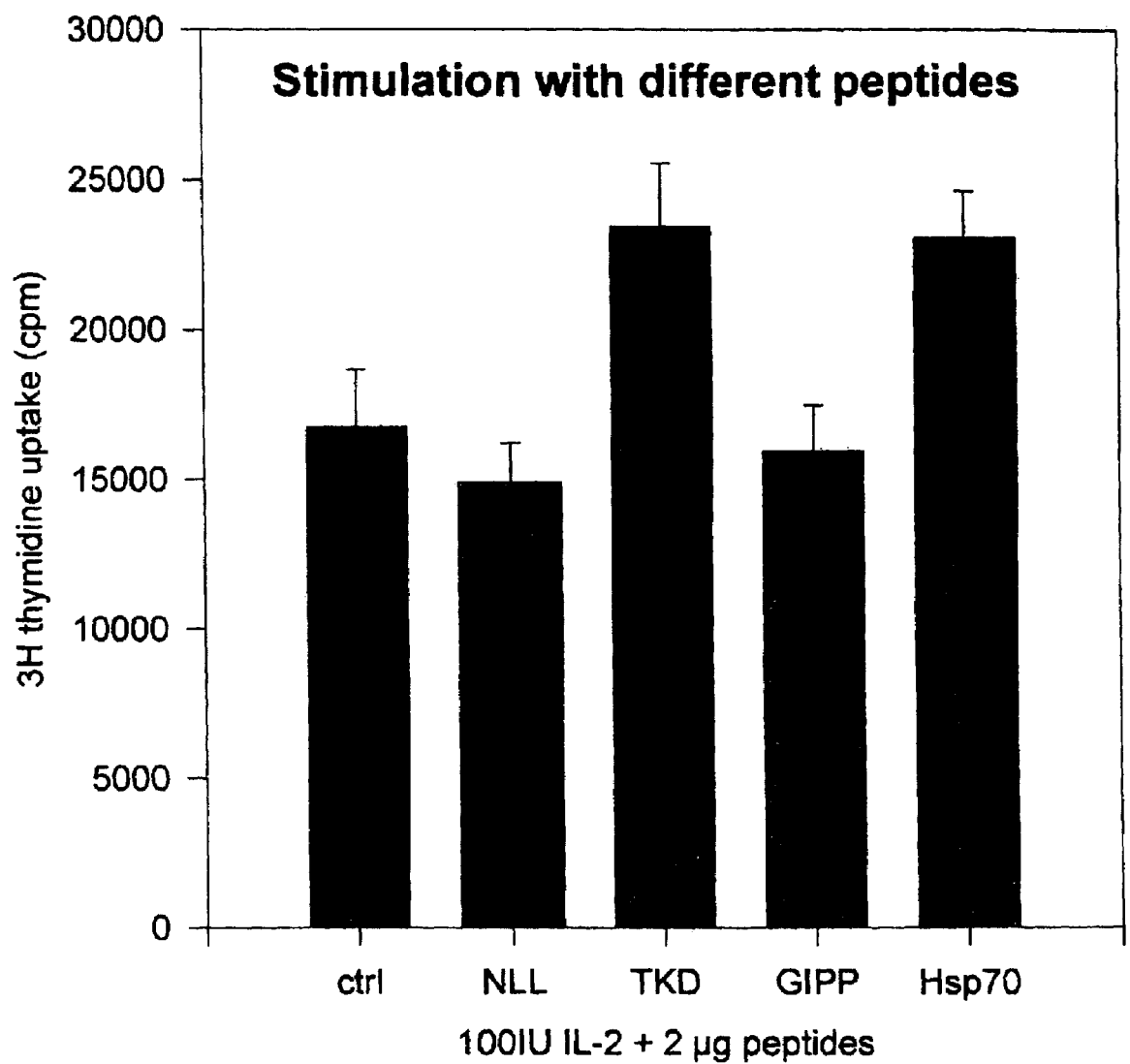
Figure 1E:
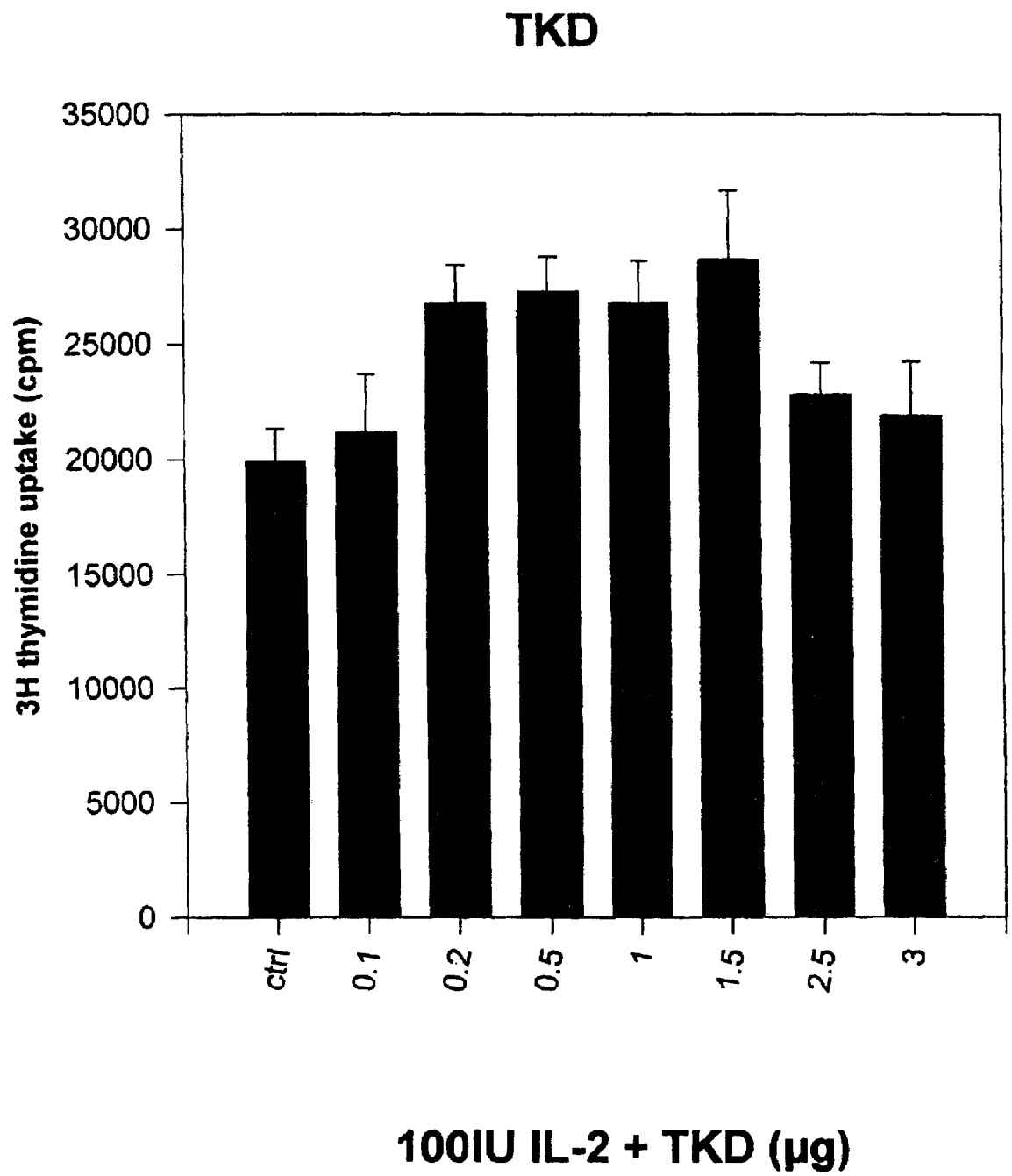
Figure 1F:
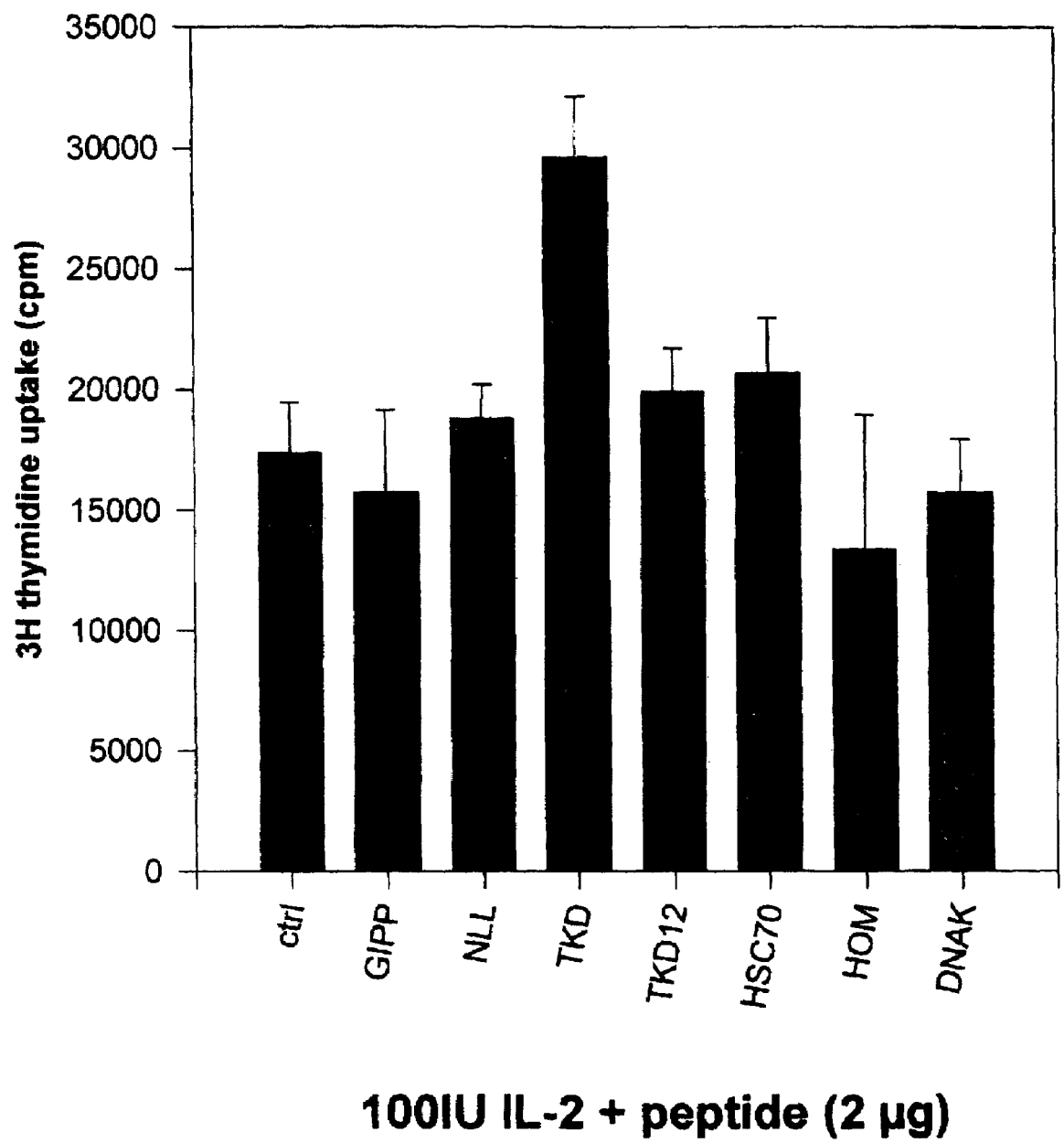

Comparison of the proliferative response of NK cells against Hsp70 peptides. NK cells were stimulated either with IL-2 (100 IU/ml) alone or with IL-2 plus peptides NLL (8-mer, FIG. 1a), TKD (14-mer, FIG. 1b) and GIPP (13 mer, FIG. 1c) at concentrations 0.02, 0.2, 2, 4 and 8 µg/ml. As a positive control NK cells were stimulated with rHsp70 protein at a concentration of 10 µg/ml. The proliferative response of NK cells was measured 72 h after peptide incubation and an 18 h incubation period with $^3$H thymidine (1 µpCi/ml). Stimulation with different peptides at a concentration of 2 µg peptide per ml is shown in FIG. 1d. In FIG. 1e stimulation with TKD in a more refined scale between 0.1 and 3 µg is shown. FIG. 1f shows stimulation with various peptides. Values are given as the means of four independent experiments +/−SD.

FIG. 2.

Figure 2A:
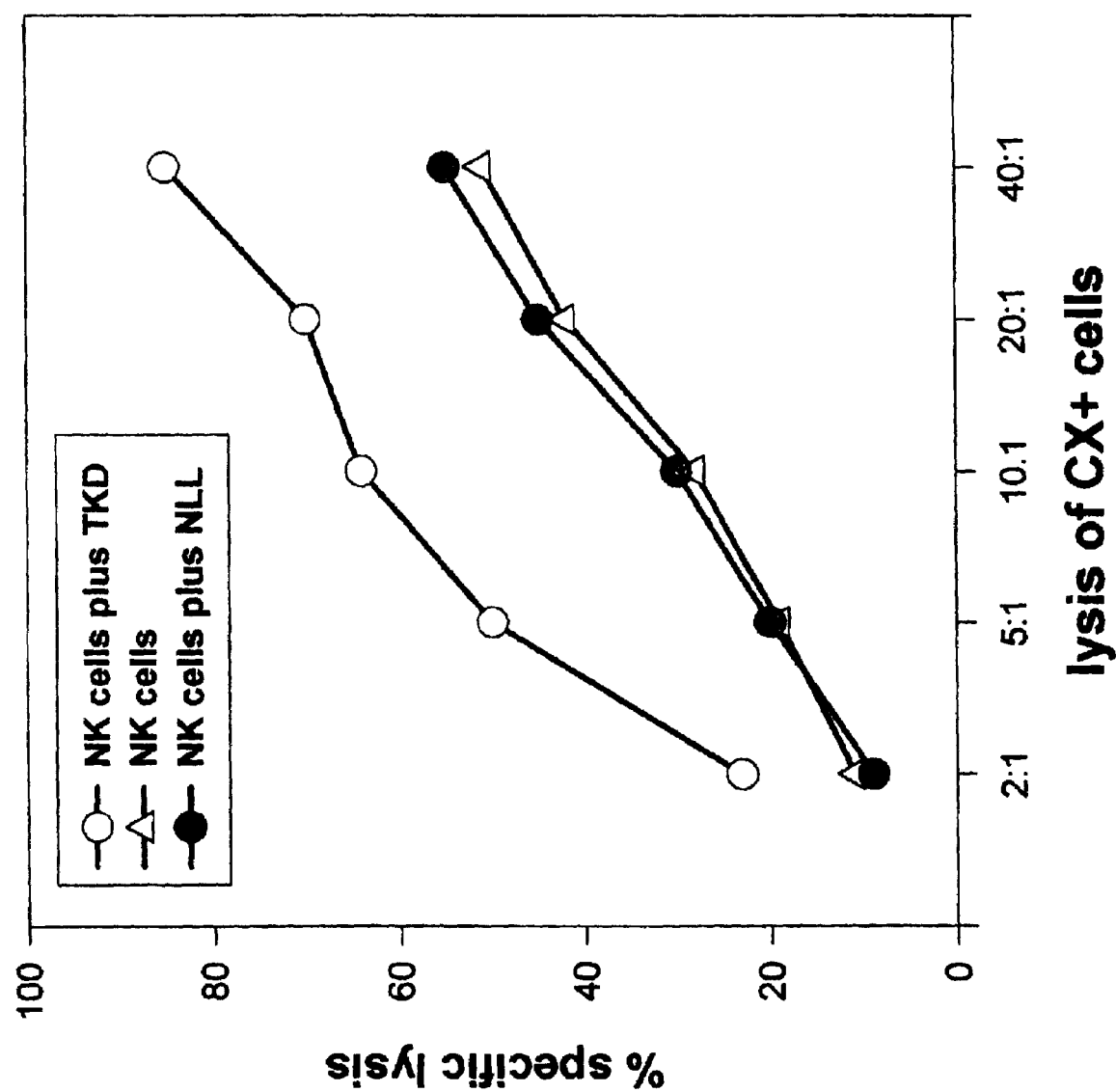
Figure 2B:
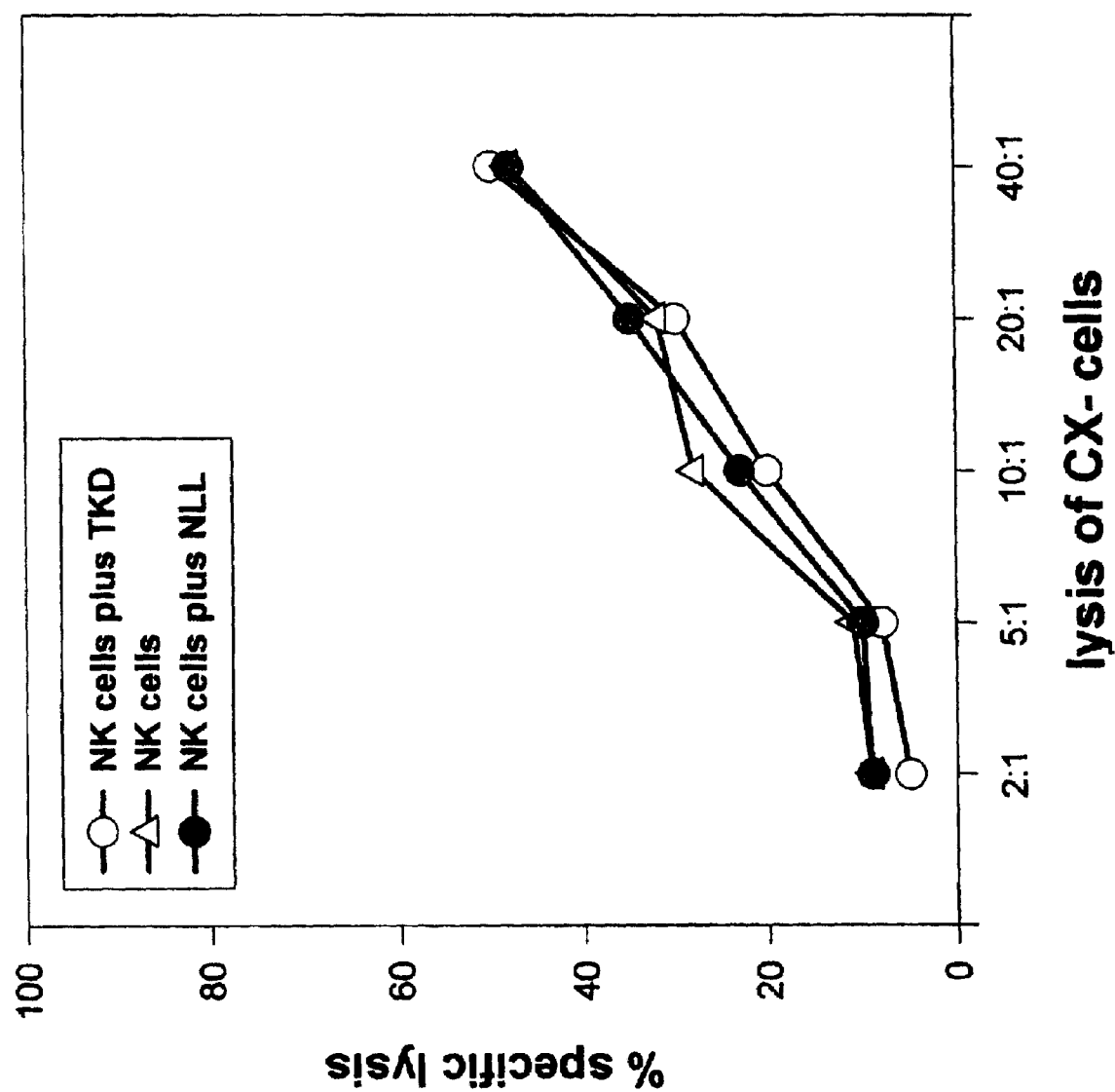

Cytolytic activity of NK cells stimulated with IL-2 alone or with IL-2 plus the 14-mer peptide TKD or with IL-2 plus the 8-mer peptide NLL. Cytolytic activity of NK cells either stimulated with low dose IL-2 (100 IU/ml) alone or with IL-2 plus the 14-mer peptide TKD (2 µg/ml) or with IL-2 plus the 8-mer peptide NLL (2 µg/ml) for 4 days. As target cells $^{51}$Cr labeled CX+ (FIG. 2a) and CX− (FIG. 2b) tumor cells, that differ with respect to their capability to express Hsp70 on the plasma membrane, were used. The results are expressed as the percentage of specific lysis at varying E:T ratios ranging from 2:1 up to 40:1. The percentage spontaneous release for each tumor target cell line was less than 20%. A phenotypic characterization of the NK cells reveals the following: NK cells plus TKD: CD3, 6%; CD16/56, 79%; NK cells plus NLL: CD3, 8%; CD16/56 80%; NK cells: CD3, 5%; CD16/56:81%.

The data represent one representative experiment out of three.

A better understanding of the present invention and of its many advantages will be had from the following examples, given by way of illustration.

EXAMPLE 1

Epitope Mapping Analysis of the Hsp70 Specific mAb

Previously, we showed an unusual plasma membrane localization of Hsp70 selectively on tumor cells with the Hsp70 specific mAb RPN1197 (Multhoff et al., 1995a/b; Botzler at al., 1996; Multhoff et al., 1997). This antibody also has been found to inhibit the cytolytic activity of cells against Hsp70 expressing tumor cells (Multhoff et al., 1995b). By using Hsp70 deletion mutants that either lack the C- or the N-terminal domain the binding epitope of the mAb RPN1197 could be localized within the C-terminal substrate binding domain of Hsp70 between aa 428-618 (Botzler et al., 1998). Due to the fact that RPN1197 exhibits an inhibitory effect on the cytolytic activity of NK cells against Hsp70 expressing tumor cells it was of interest to map the binding epitope. By peptide scanning (pepscan) of the C-terminal substrate binding domain within aa 384-618 the 8-mer peptide NLLGRFEL (aa 454-461) could be determined as the relevant recognition structure for the mAb RPN1197 (Table Ia).

TABLE I a

Results of the pepscan analysis of the C-terminal domain of Hsp70 protein (aa 384-618); 13-mer peptides with an overlap of 11 peptides were tested.

| positive pepspots | Sequence region aa 444-471 of Hsp70 protein | |
|---|---|---|
| aa 444-471 | SEQ ID NO:4  | EGERAMTKDNNLLGRFELSGIPPAPRGV |
| aa 444-456 | SEQ ID NO:5  | EGERAMTKDNNLL |
| aa 446-458 | SEQ ID NO:6  | --ERAMTKDNNLLGR |
| aa 448-461 | SEQ ID NO:7  | ----AMTKDNNLLGRFEL |
| aa 450-463 | SEQ ID NO:8  | ------TKDNNLLGRFELSG |
| aa 452-465 | SEQ ID NO:9  | --------DNNLLGRFELSGIP |
| aa 454-467 | SEQ ID NO:10 | ----------NLLGRFELSGIPPA |
| aa 456-469 | SEQ ID NO:11 | ------------LGRFELSGIPPAPR |
| aa 458-471 | SEQ ID NO:12 | --------------RFELSGIPPAPRGV |

The region 444-471 is shown; positive pepspots are marked in bold.

EXAMPLE 2

Analysis of the Immunostimulatory Capacity of Different Hsp70 Peptides

An incubation of NK cells with low dose IL-2 (100 IU/ml) plus recombinant human Hsp70 protein (rHsp70) or the C-terminal domain of Hsp70hom has been found to increase the proliferative response of human NK cells, as compared to NK cells that had been stimulated with IL-2 only (Multhoff et al. 1999). In an effort to define the minimal immunostimulatory sequence within the C-terminal domain of Hsp70, three peptides have been synthesized. Based on the 8-mer antibody binding epitope (NLLGRFEL) of RPN1197 mAb, a C-(GIPP) and an N-terminal (TKD) extended peptide were produced to test them in a standard $^3$H thymidine uptake assay. The C- and N-terminal extensions were in accordance to the primary sequence of human Hsp70 (Table I b).

TABLE I b

Amino acid (aa) sequences of peptides that were used for NK Stimulation assays.

| Origin of Protein | aa | Sequence | Name (Length) |
|---|---|---|---|
| Hsp70 | 454-461 SEQ ID NO:13 | ----NLLGRFEL | NLL (8-mer) |
| Hsp70 | 454-466 SEQ ID NO:14 | ----NLLGRFELSGIPP | GIPP (13-mer) |
| Hsp70 | 450-463 SEQ ID NO:8 | TKDNNLLGRFELSG | TKD (14-mer) |

As an internal control the proliferative capacity of NK cells against intact recombinant Hsp70 protein (rHsp70) was investigated. A concentration of 10 µg/ml of rHsp70 has been defined as an optimal stimulatory dose, previously (loc. sit). With respect to the molecular weight of the different peptides the concentration which is equivalent to 10 µg full length Hsp70 protein (72 kba) was calculated as 0.2 µg/ml for TKD (1563 Da) and GIPP (1452 Da) and as 0.1 µg/ml for NLL (942 Da). With respect to these results all peptides were tested at a concentration range of 0.02 µg up to 8 µg/ml. As shown in FIG. 1 the 8-mer peptide NLL and the C-terminal extended peptide GIPP did not stimulate the proliferative capacity of NK cells at any of the tested peptide concentrations. However, the N-terminal extended 14-mer peptide TKD exhibits a comparable immunostimulatory capacity like full length Hsp70 protein at a concentration range between 0.2 up to 2 µg/ml. This peptide concentration is comparable to a concentration of 10-100 µg/ml of full length Hsp70 protein.

The proliferative response of T cells derived from the same donors was also tested against the peptides plus low dose IL-2 (100 IU/ml). As expected none of the three peptides NLL, GIPP or TKD stimulates T cell growth at any of the tested concentrations (data not shown). However, experiments are in progress investigating the immune response of T cells against complexes consisting of rHsp70 protein and the Hsp70 peptides NLL, GIPP, TKD.

Since TKD appears to stimulate the proliferative activity of NK cells the question arises whether this peptide, similar to Hsp70 protein, also stimulates the cytolytic activity. The role of Hsp70 membrane expression as a tumor specific recognition structure for the cytolytic activity of NK cells was demonstrated with HLA identical colon carcinoma sublines CX+ and CX− that differ profoundly with respect to their capacity to express Hsp70 on the plasma membrane-(14). In the present study the cytolytic response of NK cells stimulated for 4 days either with IL-2 alone (100 IU/ml) or with IL-2 plus NLL or IL-2 with TKD peptide (2 µg/ml) were compared. A phenotypic characterization of the effector cells was performed directly before stimulation and on day 4 after stimulation. The results are shown in the legend of FIG. 2. IL-2 plus TKD stimulated NK cells exhibited a significantly enhanced lytic activity against Hsp70 expressing CX+ tumor cells compared to NK cells that were stimulated either with IL-2 alone or with IL-2 plus NLL peptide. However, no significant differences in lysis of CX− tumor cells was observed after stimulation with either of the peptides. This finding indicates that the immunostimulatory effects of the 14-mer TKD peptide on NK cells is Hsp70 specific.

EXAMPLE 3

Comparison of NK Stimulatory and Non-Stimulatory Hsp70 Peptides and Protein Sequences A comparison of the 14-mer stimulatory peptide sequence (TKD) of Hsp70 (indicated in bold) with the adequate region of Hsp70hom reveals one conservative amino acid exchange at position 462 from serin (S) to threonin (T) as shown in Table II.

of importance since only Hsp70 but not Hsc70 is able to activate NK cells. Furthermore, this aa exchange might be responsible for the specificity of the Hsp70 specific antibody RPN1197. This antibody is known to react with Hsp70 but does not cross-react with Hsc70. The only aa difference of Hsp70 and Hsc70 within the 8-mer antibody binding epitope (aa 454-460) is the exchange at position 458 from arginine (R) to lysine (K).

TABLE II

Comparison of the amino acid (aa) sequences of peptides and proteins with NK-stimulatory and non-stimulatory capacity.

| origin | aa | sequence | NK cell stimulation |
|---|---|---|---|
| Hsp70 (peptide) | 454-461 SEQ ID NO:13 | - - - - N L L G R F E L (8 mer peptide) | no |
| Hsp70 (peptide) | 454-466 SEQ ID NO:14 | N L L G R F E L S G I P P (13 mer peptide) | no |
| Hsp70 (peptide) | 450-463 SEQ ID NO:8 | T K D N N L L G R F E L S G (14 mer peptide) | yes |
| Hsp70 (peptide) | 441-463 SEQ ID NO:15 | E G ERA M T K D N N L L G R F E L S G (20 mer peptide) | yes |
| Hsp70hom (complete protein) | 450-463 SEQ ID NO:16 | T K D N N L L G R F E LTG (complete protein) | yes |
| Hsc70 (complete protein) | 450-463 SEQ ID NO:17 | T K D N N L L G K F E LTG (complete protein) | no |
| Dank (complete protein) | 447-460 SEQ ID NO:18 | A A D N K S L G Q F N L D G (complete protein) | no |

Since, both proteins Hsp70 and Hsp70hom and the 14-mer peptide TKD are able to stimulate NK cells the aa at position 462 seems to be not relevant for the stimulation Of NK cells. In contrast, the conservative aa exchange at position 458 from arginine (R) to lysine (K) between Hsp70 and Hsc70 might be In a further experiment that was scheduled as outlined above, only peptides were tested for their capacity to stimulate NK cells, see Table III, below. All these experiments allow the conclusion that amino acids TKDN in positions 450 to 453, R in position 458 and S in position 462 are crucial for the effectiveness of the peptide.

TABLE III

Comparison of the amino acid (aa) sequences only of peptides (but not proteins) with NK-stimulatory and non-stimulatory capacity. The immunostimulatory capacity of the different peptides was determined in 3H thymidine uptake assays and 51Cr release assays.

| origin | aa | sequence | NK cell stimulation |
|---|---|---|---|
| Hsp70 (NLL) | 454-461 SEQ ID NO:13 | - - - - N L L G R F E L | no |
| Hsp70 (GIPP) | 454-466 SEQ ID NO:14 | - - - - N L L G R F E L S G I P P | no |
| Hsp70 (TKD) | 450-463 SEQ ID NO:8 | T K D N N L L G R F E L S G | yes |
| Hsp70 (TKD12) | 450-461 SEQ ID NO:19 | T K D N N L L G R F E L | no |
| Hsp70 | 445-463 SEQ ID NO:20 | G ERA M T K D N N L L G R F E L S G | yes |
| Hsp70hom (HOM) | 450-463 SEQ ID NO:16 | T K D N N L L G R F E LTG | low |

TABLE III-continued

Comparison of the amino acid (aa) sequences only of peptides (but not proteins) with NK-stimulatory and non-stimulatory capacity. The immunostimulatory capacity of the different peptides was determined in 3H thymidine uptake assays and 51Cr release assays.

| origin | aa | sequence | NK cell stimulation |
|---|---|---|---|
| Hsc70 (Hsc70) | 450-463 SEQ ID NO:17 | T K D N N L L G K F E LTG | no |
| Dnak (DNAK) | 447-460 SEQ ID NO:18 | AADNKSLGQFNLDG | no |

Amino acid exchanges to the 14-mer stimulatory peptide are indicated in bold.

CONCLUSIONS

In summary these data provide evidence that not only full length Hsp70 protein or the C-terminal domain of Hsp70hom is able to stimulate proliferation and the cytolytic activity of NK cells against Hsp70 expressing tumor cells but also a 14-mer peptide which is part of the C-terminal domain of Hsp70. The sequence of the 14mer peptide is an N-terminal extension of the 8-mer binding epitope of the Hsp70 specific antibody RPN1197. This mAb not only detects plasma membrane bound Hsp70 but also has been found to inhibit NK-mediated lysis against Hsp70-positive tumor cells. This is the first report that NK cells can be stimulated by a 14-mer peptide derived from the C-terminal region of Hsp70.

Recently, the existence of HSP specific receptors has been shown for antigen-presenting cells by internalization experiments of gold-labeled HSP and by confocal microscopy (Arnold-Schild et al., 1999; Asea et al., 2000). Functionally, we demonstrated that HSp70 specific receptors also might exist on NK cells (Multhoff et al., 1999). Investigations are in progress to answer the question whether the 14-mer peptide derived from the C-terminal domain of Hsp70 physically interacts with the Hsp70 specific receptor on NK cells.

Materials and Methods

Epitope Mapping Analysis

The monoclonal antibody RPN1197 reacts only with the inducible 72 kba HSP, and is of similar reactivity to the antibody reported by Welch and Suhan (1986). Its specificity has been confirmed by immunoprecipitation of the 72 kDa protein from heat shocked cells. Epitope mapping analysis of mAb RPN1197 was perfomed using pepspot membranes with horseradish peroxidase conjugates and chemiluminescent luminol (Jerini Bio Tools GmbH, Berlin, Germany). Cellulose bound 13-mer peptides of the C-terminal domain of Hsp70 (aa 384-618) that exhibit an overlap of 11-mer peptides were used (Reineke et al., 1996).

Hsp70 and Hsp70 Peptides

Human recombinant Hsp70 protein (rHsp70) was obtained from StressGen, Victoria, British Columbia, Canada (SPP-755). The 8-mer, 14-mer and 13-mer peptides NLLGRFEL (NLL) (SEQ ID NO:13), TKDNNLLGRFELS (TKD) (SEQ ID NO:6), NLLGRFELSGIPP (GIPP) (SEQ ID NO:14), were produced by the F-moc synthesis (fluorenylmethoxy-carbonyl/t-butyl-based solid-phase peptide chemistry method on SMPS 850 (Zinser Analytic) and ABI 488A (Perkin Elmer, Norwalk, Conn.) synthesizers. The purity of Hsp70 proteins and Hsp70 peptides was determined by the Limulus amebeocyte lysate assay (BioWhittaker, Maryland, USA).

NK c IIs

Briefly, monocyte depleted peripheral blood lymphocytes (PBL) were isolated from buffy coats of healthy human volunteers (Multhoff et al., 1995a). NK cells were purified by adherence selection following a modified protocol of Vujanovic (1993). T cells remain in the supernatant cell population.

FACScan Analysis

Directly fluorescein-conjugated mAb ($CD3^{FITc}$/CD16/$CD56^{PE}$, Becton Dickinson, Heidelberg, Germany) were added to cell suspensions ($0.1 \times 10^6$ cells), incubated for 20 min on ice, washed and analysed on a FACScan instrument (Becton Dickinson, Heidelberg, Germany). The percentage of positively stained cells was defined as the number of specifically stained, viable (propidium-iodide negative) cells minus the number of cells stained with an isotype matched control antibody on a FACScan instrument (Becton Dickinson, Heidelberg, Germany).

Tumor Cell Lines

The colon carcinoma sublines CX+ (>90% Hsp70 positive cells) and CX− (<20% Hsp70 positive cells) described in patent application EP-A2-084 300 5 and originally derived from CX2 colon carcinoma cells (Tumorzentrum Heidelberg, TZB 610005, Germany) that differ with respect to their capacity to express Hsp70 on their plasma membrane were cultured at 37° C., 5% $CO_2$ in RPMI-1640 medium (Gibco, Eggenttein, Germany) supplemented with heat-inactivated 10% FCS (Gibco) and 2 mM L-glutamine and antibiotics (penicillin/streptomycin). The cell lines were kept in culture under exponential growth conditions, and harvested with trypsin/EDTA solution. The experiments were performed between passage 10-30. All cell lines were free from mycoplasma contamination as determined by repeated testing using the 6-methylpurin desoxyribosid assay (Boehringer Mannheim, Germany).

$^3$H Thymidine Uptake Assay

The proliferative capacity of NK and T cells against different Hsp70 peptides and Hsp70 protein (loc. sit) was determined in a standard $^3$H thymidine uptake assay (22). Viable cells ($5 \times 10^4$ cells/100 µl) were seeded in 96-well flat-bottom microtiter plates (Greiner Nuertingen, Germany) in supplemented RPMI-1640 medium containing 100 IU IL-2 and Hsp70 protein (10 µg/ml) or different amounts of Hsp70 peptides ranging from 0.02 up to 10 µg/ml. As an internal control the proliferation against IL-2 alone was measured in parallel. After a 24 or 48 hour incubation period the cells were pulsed with $^3$H thymidine (1 µCi/well) and the total uptake was measured following an 18 hour incubation period at 37° C. in a liquid scintillation counter (Beckmann instruments, Munich, Germany).

Cell Mediated Lympholysis Assay (CML)

The cytolytic activity of NK cells was monitored in a standard $^{51}$Cr assay (23). Dilutions of the effector cells were incubated with $^{51}$Cr-labeled (100 µCi of Na$^{51}$ CrO$_4$, NEN-Dupont, Boston, Mass.) tumor target cells (3×10$^3$ cells per well) in duplicates at a final volume of 200 µl RPMI-1640 medium supplemented with 10% FCS at 37° C. for 4 h in 96-well U-bottom plates (Greiner, Nuertingen, Germany). After the incubation period supernatants were collected and the radioactivity was counted in a γ-counter (Packard Instruments). The percentage of specific lysis was determined according to the equation: (experimental release—spontaneous release)/(maximum release—spontaneous release)×100. The percentage spontaneous release was always <15% for each target cell line.

REFERENCES

Altmeyer et al., 1996, *Int J. Cancer* 69:340.
Arnold-Schild et al., 1999, *J. Immunol.* 162:3757.
Asea et al., 2000, *Nat. Med.* 6:435.
Banerjee et al., 1996, *Biopolymers* 39:769.
Barry et al., 1995, *Nature* 377:632.
Benkirane et al., 1996, *J. Biol. Chem.* 271:33218.
Berry et al., 1994, *Biochem. Soc. Trans.* 22:1033.
Botzlet et. al., 1996a, *Cancer Immunol. Immunother.* 43:226.
Botzler et al., 1996b, *Int J. Cancer* 65:633.
Botzler et al., 1998, *Cell Stress & Chaperones* 3:6.
Boyer et al., 1997, *Nat. Med.* 3:526.
DeNagel and Pierce, 1992, *Immunol. Today* 13:86.
Dorner et al., 1996, *Bioorg. Med. Chem.* 4:709.
Engelhard et al., 1994, *Proc. Nat Acad. Sci. USA* 91:3224.
Fassina et al., 1994, *Immunomethods* 5:114.
Ferrarini et al., 1992, *Int. J. Cancer* 51:613.
Fynan et al., 1993, *Proc. Natl. Acad. Sci. U.S.A.* 90:11478-11482.
Hartl et al., 1996, *Nature* 381: 571.
Hoffman et al., 1995, *Comput. Appl. Biosci.* 11:675.
Holzgrabe and Bechtold (2000). Deutsche Apotheker Zeitung 140(8), 813-823.
Kubinyi, H. (1993). Hausch-Analysis and Related Approaches. VCH-Verlag, Weinheim.
Lindquist and Craig, 1988. *Annu. Rev. Genet* 22:631.
Luke et al., 1997, *J. Inf. Dis.* 175:91.
MacDonald et al., 1974, *J. Exp. Med.* 140:718.
MacGregor et al., 1998, *J. Infect. Dis.* 178:92.
Montgomery et al., 1993, *DNA Cell Biol.* 12:777.
Mor, 1998, *Biochem. Pharmacol* 55:1151.
Multhoff et al., 1995a, *Blood* 86:1374.
Multhoff et al., 1995b. *Int. J Cancer* 61:272.
Multhoff et al., 1997, *J. Immunol.* 158:4341.
Multhoff et al., 1999, *Exp. Hematology* 27:1627.
OlszeWski et al., 1996. *Proteins* 25:286.
Ostresh et al., 1996, *Methods in Enzymology* 267:220.
Pabo et al., 1986, *Biochemistry* 25:5987.
Piselli et al., 1995, *J. Biol. Regul. Homeost Agents* 9:55.
Rose et al., 1996, *Biochemistry* 35:12933.
Rutenber et al., 1996, *Bioorg. Med. Chem.* 4:1545.
Schild et al., 1999, *Current Opinion in Immunology* 11:109.
Smith et al., 1983, *J. Virol.* 46:574
Srivastava et al., 1998, *Immunity* 8:657.
Strong et al., 1973, *J. Immunol. Methods* 2:279.
Tamura et al., 1993, *J. Immunol.* 151:5516.
Tamura et al., 1997, *Science* 278:117.
Tighe et al., 1998, *Immunology Today* 19:89.
Vujanovic et al., 1993, *Cell. Immunol.* 151:133.
Webster et al., 1994, *Vaccine* 12:1495-1498.
Welch et al., 1986, *J. Cell Biol.* 103:2035.
Wodak. 1987. *Ann. N.Y. Acad. Sci.* 501:1.
Xu and Liew, 1995, Immunology 84:173.
Zhang et al., 1996, *Biochem. Biophys. Res. Commun.* 224: 327.
Zhong et al., 1996, *Eur. J. Immunol.* 26:2749.

The invention claimed is:

1. An isolated peptide of at least 13 and no more than 30 amino acids in length comprising an amino acid sequence selected from the group consisting of a) TKDNNLLGRFELSG corresponding to amino acid residues 450 to 463 of SEQ ID NO:8 wherein Ser can also be Thr and b) an amino acid sequence which deviates from the amino acid sequence of (a) by way of amino acid substitution, insertion, or deletion wherein amino acids TKDN corresponding to positions 450 to 453 of SEQ ID NO:8 and the amino acid Ser which can also be Thr are retained, wherein said peptide stimulates natural killer cell activity.

2. The peptide of claim 1 comprising or having the amino acid sequence EGERAMTKDNNLLGRFELXG (SEQ ID NO: 3) wherein X is T or S or a fragment or derivative thereof.

3. A fusion (poly)peptide comprising the peptide of claim 1 or 2.

4. A composition comprising the peptide of claim 1 or 2 or a fragment or derivative thereof and a pharmaceutically acceptable carrier and/or diluent.

5. A composition comprising the fusion protein of claim 3 and a pharmaceutically acceptable carrier and/or diluent.

6. The composition of claim 4 further comprising Interleukin 2.

7. The composition of claim 5 further comprising Interleukin 2.

8. An isolated peptide of at least 13 and no more than 30 amino acids in length comprising amino acid TKDNNLLGRFELSG corresponding to amino acid residues 450 to 463 of SEQ ID NO:8 wherein Ser can also be Thr.

9. A composition comprising the peptide of claim 8 and a pharmaceutically acceptable carrier and/or diluent.

10. The composition of claim 8 further comprising Interleukin 2.

11. A fusion (poly)peptide comprising the peptide of claim 8.

12. A composition comprising the fusion (poly)peptide of claim 11 and a pharmaceutically acceptable carrier and/or diluent.

* * * * *

UNITED STATES PATENT AND TRADEMARK OFFICE
CERTIFICATE OF CORRECTION

| | | |
|---|---|---|
| PATENT NO. | : 7,517,948 B2 | Page 1 of 1 |
| APPLICATION NO. | : 10/380408 | |
| DATED | : April 14, 2009 | |
| INVENTOR(S) | : Gabriele Multhoff | |

It is certified that error appears in the above-identified patent and that said Letters Patent is hereby corrected as shown below:

IN THE TITLE PAGE:

Item (73) in the Assignee, line 1 in the name of the Assignee please replace "Multimmune" with --multimmune--; and in the address of the Assignee please replace "Regensburg" with --Munich--.

Signed and Sealed this

First Day of September, 2009

David J. Kappos
*Director of the United States Patent and Trademark Office*